(12) United States Patent
Iwane

(10) Patent No.: US 12,714,288 B2
(45) Date of Patent: Aug. 25, 2026

(54) ENDOSCOPE SYSTEM AND OPERATION METHOD FOR ENDOSCOPE SYSTEM

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 257 days.

(21) Appl. No.: 18/448,396

(22) Filed: Aug. 11, 2023

(65) Prior Publication Data

US 2023/0380660 A1 Nov. 30, 2023

Related U.S. Application Data

(63) Continuation of application No. PCT/JP2021/045673, filed on Dec. 10, 2021.

(30) Foreign Application Priority Data

Feb. 12, 2021 (JP) ................................ 2021-021030

(51) Int. Cl.
*A61B 1/00* (2006.01)

(52) U.S. Cl.
CPC ........ *A61B 1/0002* (2013.01); *A61B 1/00006* (2013.01); *A61B 1/000094* (2022.02);
(Continued)

(58) Field of Classification Search
CPC ............ A61B 1/00002; A61B 1/00004; A61B 1/00009; A61B 1/000094;
(Continued)

(56) References Cited

U.S. PATENT DOCUMENTS

2008/0024599 A1* 1/2008 Hirakawa .......... A61B 1/00009 348/65
2016/0128545 A1* 5/2016 Morita ................ A61B 1/0005 600/109

(Continued)

FOREIGN PATENT DOCUMENTS

CN 105555180 A 5/2016
JP H10-323326 A 12/1998

(Continued)

OTHER PUBLICATIONS

International Search Report issued in PCT/JP2021/045673; mailed Mar. 8, 2022.

(Continued)

*Primary Examiner* — Ryan N Henderson
*Assistant Examiner* — Pamela F Wu
(74) *Attorney, Agent, or Firm* — Studebaker Brackett PLLC

(57) ABSTRACT

An endoscope system includes an endoscope, which includes an instruction unit that issues a selection condition switching instruction and a still image storage instruction and which images a subject, and a processor. The processor acquires an endoscope image for each frame, temporarily stores the endoscope image selected based on a first selection condition or a second selection condition in a temporary storage area, performs image evaluation to assign an image evaluation value for each of the temporary storage images, and stores, based on the still image storage instruction, an optimal still image selected in accordance with the image evaluation value.

18 Claims, 19 Drawing Sheets

(52) U.S. Cl.
CPC .... *A61B 1/000095* (2022.02); *A61B 1/00045* (2013.01); *A61B 1/00055* (2013.01)

(58) Field of Classification Search
CPC ........ A61B 1/000095; A61B 1/000096; A61B 1/0002; A61B 1/00045; A61B 1/00188; A61B 1/04; A61B 1/045
USPC ......... 600/109, 160, 167, 117–118, 163, 103
See application file for complete search history.

(56) References Cited

U.S. PATENT DOCUMENTS

| | | | | |
|---|---|---|---|---|
| 2017/0034484 | A1* | 2/2017 | Yanagidate | A61B 1/000095 |
| 2017/0280986 | A1* | 10/2017 | Sekowski | H04N 23/56 |
| 2018/0310812 | A1* | 11/2018 | Kuriyama | A61B 1/00188 |
| 2022/0202284 | A1* | 6/2022 | Tachibana | A61B 1/00006 |

FOREIGN PATENT DOCUMENTS

| | | |
|---|---|---|
| JP | 2011-218090 A | 11/2011 |
| JP | 2013-230319 A | 11/2013 |
| JP | 2020-168164 A | 10/2020 |

OTHER PUBLICATIONS

International Preliminary Report on Patentability (Chapter I) and Written Opinion of the International Searching Authority issued in PCT/JP2021/045673; issued Aug. 15, 2023.
Office Action issued in CN 202180093512.5; mailed by the State Intellectual Property Office of the People's Republic of China on Jan. 26, 2026.
"Notice of Reasons for Refusal" Office Action issued in JP 2022-581207; mailed by the Japanese Patent Office on Nov. 18, 2025.

* cited by examiner

FIG. 2

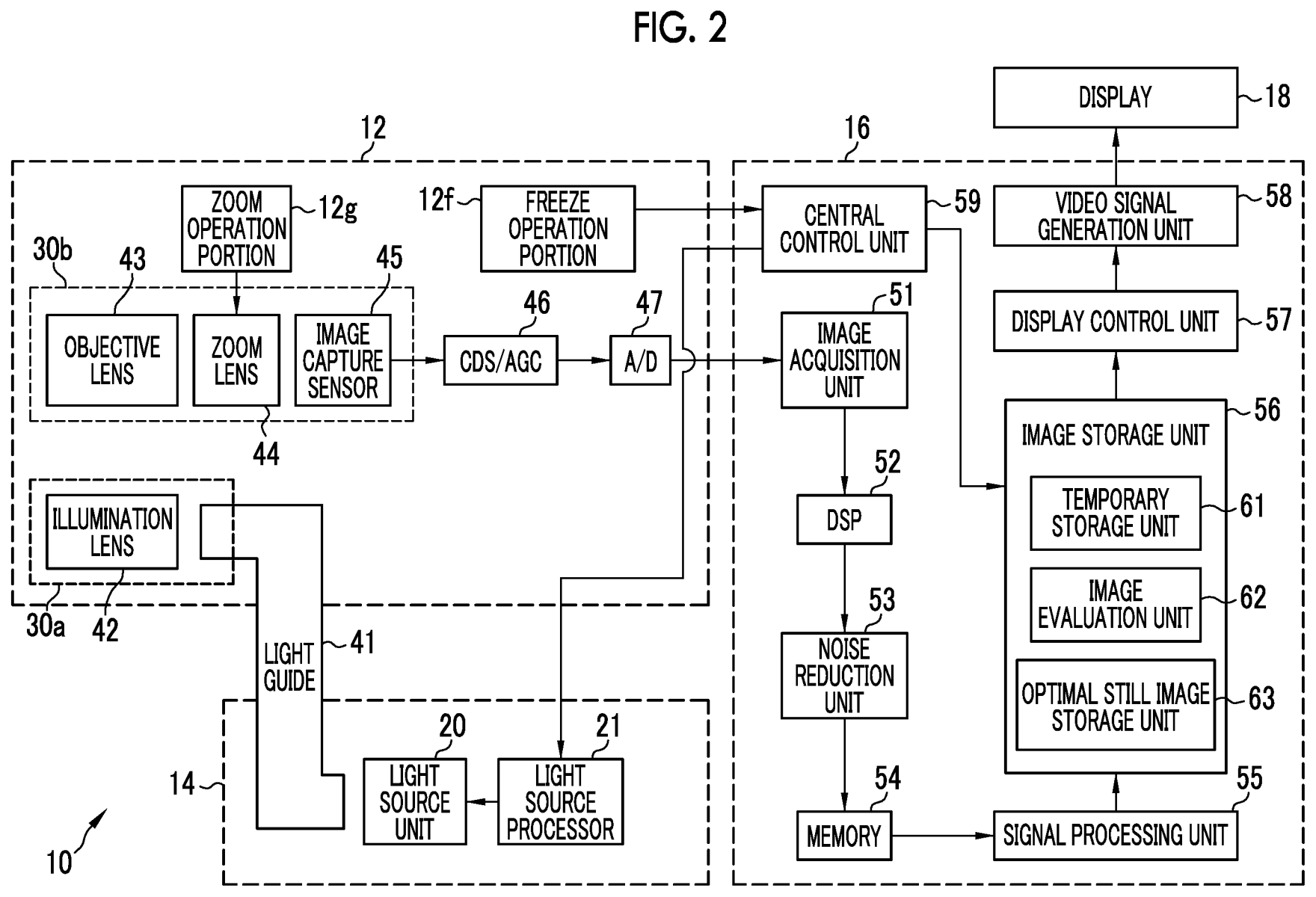

10
12
12g ZOOM OPERATION PORTION
12f FREEZE OPERATION PORTION
30b
43 OBJECTIVE LENS
44 ZOOM LENS
45 IMAGE CAPTURE SENSOR
46 CDS/AGC
47 A/D
30a
42 ILLUMINATION LENS
41 LIGHT GUIDE
14
20 LIGHT SOURCE UNIT
21 LIGHT SOURCE PROCESSOR
16
59 CENTRAL CONTROL UNIT
51 IMAGE ACQUISITION UNIT
52 DSP
53 NOISE REDUCTION UNIT
54 MEMORY
55 SIGNAL PROCESSING UNIT
56 IMAGE STORAGE UNIT
61 TEMPORARY STORAGE UNIT
62 IMAGE EVALUATION UNIT
63 OPTIMAL STILL IMAGE STORAGE UNIT
57 DISPLAY CONTROL UNIT
58 VIDEO SIGNAL GENERATION UNIT
18 DISPLAY 82
83
84
18
81

ENDOSCOPE SYSTEM AND OPERATION METHOD FOR ENDOSCOPE SYSTEM

CROSS-REFERENCE TO RELATED APPLICATIONS

This application is a Continuation of PCT International Application No. PCT/JP2021/045673 filed on 10 Dec. 2021, which claims priority under 35 U.S.C § 119(a) to Japanese Patent Application No. 2021-021030 filed on 12 Feb. 2021. The above application is hereby expressly incorporated by reference, in its entirety, into the present application.

BACKGROUND OF THE INVENTION

1. Field of the Invention

The present invention relates to an endoscope system that stores a still image and an operation method for an endoscope system.

2. Description of the Related Art

In the medical field, diagnosis using an endoscope system that comprises an endoscope and a processor device has been widely performed. By using the endoscope system, an image (hereinafter, referred to as an endoscope image) obtained by imaging an observation target as a subject with an endoscope can be stored as a still image. The still image is used for display on a display, attachment to a medical report, or the like and is useful for diagnosis.

In many cases, endoscopes cannot use, for example, a camera shake correction function or the like provided in a general video camera or a digital camera because the endoscope has limitations on a size, a distance between the endoscope and the subject is short, or the like. In that respect, as the endoscope system, an endoscope system that can display a still image with proper brightness and no blur by storing a captured image that has been evaluated for brightness and blur is known (JP2020-168164A).

SUMMARY OF THE INVENTION

An endoscope does not have an autofocus function in many cases. In this case, in order to acquire an in-focus still image, a user himself/herself operates the endoscope to adjust the distance to the subject, thereby obtaining a still image with the optimum focus. However, as shown in FIG. 20, since a subject of the endoscope is an organ, a subject 91 may move by, for example, a distance dm because of pulsation, peristalsis, or the like at a timing when the user appropriately adjusts a distance between a distal end portion of an endoscope 12 and the subject 91 to a distance db and fixes the endoscope in focus. As a result, the distance between the endoscope 12 and the subject 91 becomes a distance db+c, which causes the distance to be separated from the in-focus distance db and an image to be obtained to be out of focus. As described above, there may be a case where an imaging situation, such as the distance to the subject, unexpectedly changes, which makes it difficult to obtain a still image with the optimum focus.

In response to this, it is also conceivable to automatically acquire a plurality of still images at a plurality of timings and select an in-focus still image from among the plurality of still images. However, in this method, since a large amount of still images at unintended timings are stored and the like, it may be difficult to select a still image with the proper focus or the like, and a memory capacity for storing still images may increase.

An object of the present invention is to provide an endoscope system and an operation method for an endoscope system capable of easily acquiring an optimum still image in response to a change in an imaging situation.

The present invention relates to an endoscope system comprising: an endoscope that images a subject; and a processor, in which the endoscope includes an instruction unit, the processor is configured to: acquire an endoscope image obtained by imaging the subject with the endoscope for each frame; temporarily store the endoscope image selected based on a first selection condition or a second selection condition in a temporary storage area; perform image evaluation to assign an image evaluation value for each of the temporary storage images temporarily stored in the temporary storage area; switch between the first selection condition and the second selection condition based on a selection condition switching instruction; and store, based on a still image storage instruction, an optimal still image selected in accordance with the image evaluation value from the temporary storage images, and the instruction unit is configured to issue the selection condition switching instruction and the still image storage instruction.

It is preferable that the processor is configured to, in a case where acquisition of the endoscope image is started, temporarily store the endoscope image selected based on the first selection condition.

It is preferable that the instruction unit is configured to perform a first operation and a second operation and issue the still image storage instruction through the second operation.

It is preferable that the instruction unit includes a momentary type switch, and the first operation is pressing of the momentary type switch, and the second operation is releasing of the pressed momentary type switch.

It is preferable that the instruction unit includes an alternate type switch, and the first operation is first pressing and releasing of the alternate type switch, and the second operation is second pressing and releasing of the alternate type switch.

It is preferable that the processor is configured to measure a period from the first operation to the second operation, and the instruction unit is configured to, in a case where the period is equal to or longer than a determination period set in advance, issue the selection condition switching instruction when the determination period has elapsed from the first operation.

It is preferable that the instruction unit is configured to issue the selection condition switching instruction in a case where the endoscope image is temporarily stored based on the second selection condition by the processor when the still image storage instruction is issued.

It is preferable that the processor is configured to temporarily store the selected endoscope image in the temporary storage area in a number equal to or less than a maximum number set in advance as the temporary storage image, and the first selection condition includes, as a first A selection condition, in a case where the temporary storage image is temporarily stored in the temporary storage area in a number less than the maximum number, temporarily storing the endoscope image in the temporary storage area as the temporary storage image in an order of most recent imaging time until the maximum number is reached and, as a first B selection condition, in a case where the maximum number of temporary storage images are temporarily stored in the temporary storage area, deleting the temporary storage image with an oldest imaging time, among the temporary storage images temporarily stored in the temporary storage area, from the temporary storage area and then temporarily storing the endoscope image in the temporary storage area as the temporary storage image in the order of the most recent imaging time.

It is preferable that the processor is configured to temporarily store the selected endoscope image in the temporary storage area in a number equal to or less than a maximum number set in advance as the temporary storage image, and the second selection condition includes, as a second A selection condition, in a case where the temporary storage image is temporarily stored in the temporary storage area in a number less than the maximum number, temporarily storing the endoscope image in the temporary storage area as the temporary storage image in an order of most recent imaging time until the maximum number is reached and, as a second B selection condition, in a case where the maximum number of temporary storage images are temporarily stored in the temporary storage area, leaving only a proper still image selected in accordance with the image evaluation value from the temporary storage images in the temporary storage area as the temporary storage image and deleting an image except for the proper image from the temporary storage area, and then performing the second A selection condition.

It is preferable that the processor is configured to temporarily store the selected endoscope image in the temporary storage area in a number equal to or less than a maximum number set in advance as the temporary storage image, and the second selection condition includes, as a second A selection condition, in a case where the temporary storage image is temporarily stored in the temporary storage area in a number less than the maximum number, temporarily storing the endoscope image in the temporary storage area as the temporary storage image in an order of most recent imaging time until the maximum number is reached and, as a second C selection condition, in a case where the maximum number of temporary storage images are temporarily stored in the temporary storage area, leaving only a proper still image selected in accordance with the image evaluation value from the temporary storage images in the temporary storage area as the temporary storage image and deleting an image except for the proper image from the temporary storage area, and then, after selecting and temporarily storing the endoscope image with the most recent imaging time in the temporary storage area as the temporary storage image, temporarily storing only a proper still image selected in accordance with the image evaluation value from the temporary storage images temporarily stored in the temporary storage area in the temporary storage area as the temporary storage image.

It is preferable that a display configured to display the optimal still image and/or the proper still image is further provided and the display is configured to, in a case where the optimal still image and/or the proper still image is displayed, update the optimal still image and/or the proper still image and display a latest optimal still image and/or a latest proper still image.

It is preferable that the display includes a main screen and a sub screen and that the optimal still image is displayed on the main screen for a display period set in advance and is displayed on the sub screen after the display period.

It is preferable that a notification unit configured to, in a case where the display updates and displays the optimal still image and/or the proper still image, notify a user of the update is further provided.

It is preferable that the notification unit is configured to, in a case where the first selection condition and the second selection condition are switched by the processor, notify the user of the switching.

It is preferable that the notification unit is configured to not issue the notification in a case where the notification to the user is issued again within a minimum notification period set in advance.

It is preferable that the processor is configured to perform the image evaluation on contrast and/or brightness of the temporary storage image and that the image evaluation value is a value related to the contrast and/or the brightness of the temporary storage image.

It is preferable that the processor is configured to perform the image evaluation on a certainty factor and/or a malignancy degree related to a specific lesion of the subject appearing in the temporary storage image and that the image evaluation value is the certainty factor and/or the malignancy degree.

It is preferable that the processor is configured to set a threshold value for the image evaluation value, consider that the still image storage instruction is issued in a case where an image evaluation value equal to or greater than the threshold value is assigned to the temporary storage image, and store the temporary storage image to which the image evaluation value equal to or greater than the threshold value is assigned as the optimal still image.

It is preferable that the instruction unit includes a freeze operation portion.

In addition, the present invention relates to an operation method for an endoscope system including an endoscope, which includes an instruction unit and images a subject, and a processor, the operation method comprising: causing the processor to execute: acquiring an endoscope image obtained by imaging the subject with the endoscope for each frame; temporarily storing the endoscope image selected based on a first selection condition or a second selection condition in a temporary storage area as a temporary storage image; performing image evaluation to assign an image evaluation value for each of the temporary storage images temporarily stored in the temporary storage area; switching between the first selection condition and the second selection condition based on a selection condition switching instruction; and storing, based on a still image storage instruction, an optimal still image selected in accordance with the image evaluation value from the temporary storage images, in which the instruction unit is configured to issue the selection condition switching instruction and the still image storage instruction.

According to the present invention, it is possible to easily acquire an optimum still image in response to a change in an imaging situation.

BRIEF DESCRIPTION OF THE DRAWINGS

FIG. 2 is a block diagram showing a function of the endoscope system.

DESCRIPTION OF THE PREFERRED EMBODIMENTS

Figure 1:
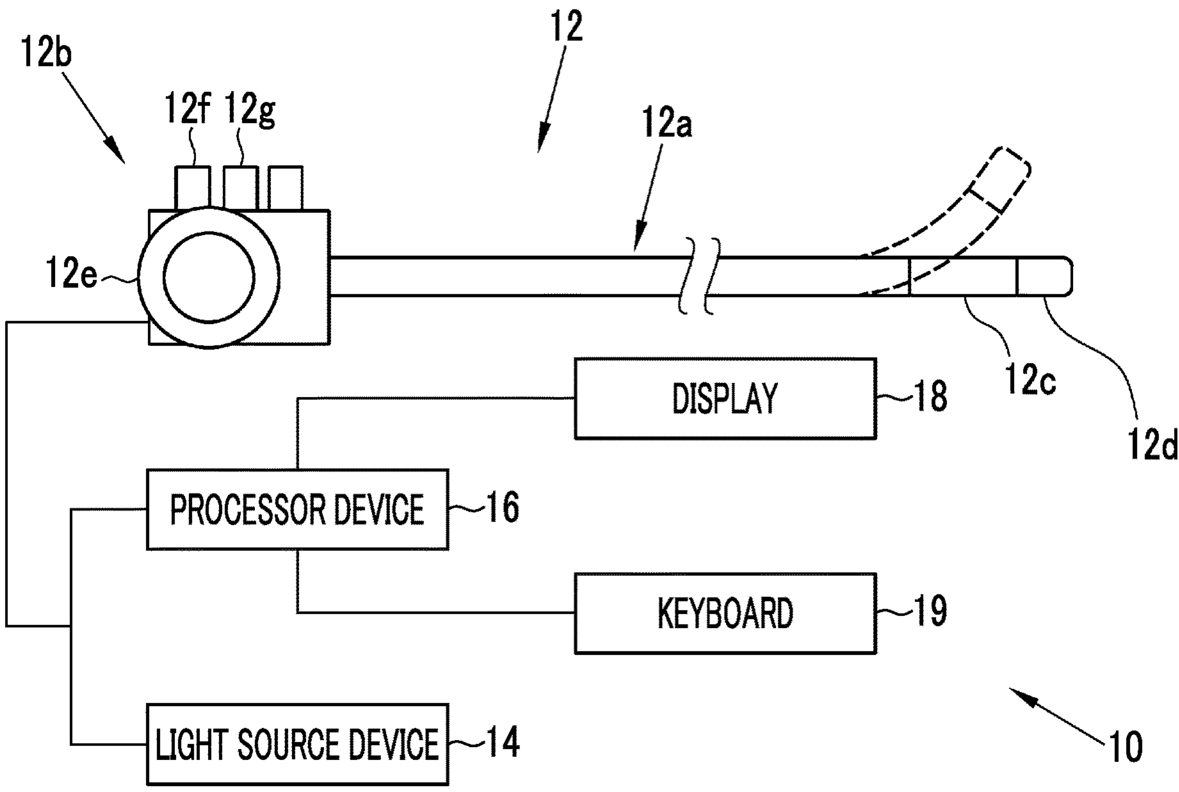
FIG. 1 is an external view of an endoscope system.

In FIG. 1, an endoscope system 10 includes an endoscope 12, a light source device 14, a processor device 16, a display 18, and a keyboard 19. The endoscope 12 is optically connected to the light source device 14 and is electrically connected to the processor device 16. The endoscope 12 includes an insertion part 12*a* to be inserted into a body of a subject to be examined having an observation target as a subject, an operation part 12*b* provided at the proximal end part of the insertion part 12*a*, and a bendable portion 12*c* and a distal end portion 12*d* that are provided on the distal end side of the insertion part 12*a*. The bendable portion 12*c* performs a bending operation by operating an angle knob 12*e* of the operation part 12*b*. The distal end portion 12*d* is directed in the desired direction by the bending operation of the bendable portion 12*c*.

The operation part 12*b* includes, in addition to the angle knob 12*e*, a freeze operation portion 12*f* for issuing a selection condition switching instruction, a still image storage instruction, or the like, which will be described below, and a zoom operation portion 12*g* for changing an image capture magnification. The still image storage instruction or the zoom operation may be performed by an operation or an instruction using a switch of the processor device 16, the keyboard 19, a foot switch (not shown), or the like, in addition to a scope switch of the freeze operation portion 12*f* or of the zoom operation portion 12*g*.

The processor device 16 is electrically connected to the display 18 and the keyboard 19. The display 18 outputs and displays, for example, an endoscope image of a video or a still image, and/or information accompanying these images. The keyboard 19 functions as a user interface that receives an input operation, such as function settings. An external recording unit (not shown) that records an image, image information, or the like may be connected to the processor device 16.

In FIG. 2, the light source device 14 emits illumination light with which the observation target is irradiated, and comprises a light source unit 20 and a light source processor 21 that controls the light source unit 20. The light source unit 20 includes, for example, a semiconductor light source, such as a plurality of colors of light emitting diodes (LEDs), a combination of a laser diode and a phosphor, or a xenon lamp or a halogen light source. In addition, the light source unit 20 includes, for example, an optical filter for adjusting the wavelength range of light emitted by the LED or the like. The light source processor 21 turns on/off each LED or the like or adjusts the drive current and the drive voltage of each LED or the like, thereby controlling the amount of illumination light. Further, the light source processor 21 changes the optical filter or the like, thereby controlling the wavelength range of illumination light.

Figure 3:
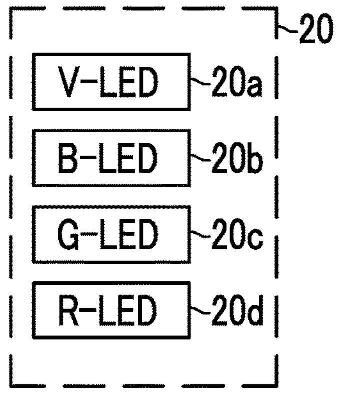
FIG. 3 is an explanatory diagram illustrating four colors of LEDs provided in a light source unit.

As shown in FIG. 3, in the present embodiment, the light source unit 20 has four colors of LEDs, that is, a violet light emitting diode (V-LED) 20*a*, a blue light emitting diode (B-LED) 20*b*, a green light emitting diode (G-LED) 20*c*, and a red light emitting diode (R-LED) 20*d*.

Figure 4:
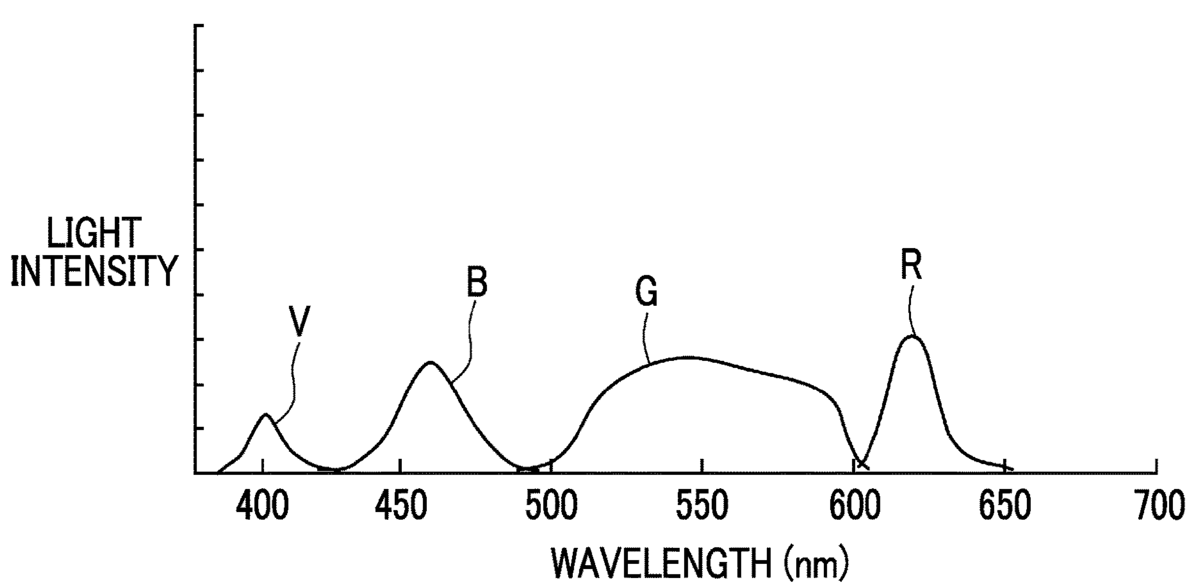
FIG. 4 is a graph showing spectra of violet light V, blue light B, green light G, and red light R.

As shown in FIG. 4, the V-LED 20*a* generates violet light V having a central wavelength of 410±10 nm and a wavelength range of 380 to 420 nm. The B-LED 20*b* generates blue light B having a central wavelength of 450±10 nm and a wavelength range of 420 to 500 nm. The G-LED 20*c* generates green light G having a wavelength range of 480 to 600 nm. The R-LED 20*d* generates red light R having a central wavelength of 620 to 630 nm and a wavelength range of 600 to 650 nm. The light source processor 21 controls the V-LED 20*a*, the B-LED 20*b*, the G-LED 20*c*, and the R-LED 20*d*. The light source processor 21 controls the respective LEDs 20*a* to 20*d* such that illumination light with different combinations of light intensity ratios between violet light V, blue light B, green light G, and red light R is emitted depending on, for example, a plurality of observation modes.

The light emitted from each of the LEDs 20*a* to 20*d* is incident on a light guide 41 via an optical path coupling portion (not shown) that includes a mirror, a lens, and the like. The light guide 41 is incorporated in the endoscope 12 and a universal cord (a cord that connects the endoscope 12 to the light source device 14 and the processor device 16). The light guide 41 propagates the light from the optical path coupling portion to the distal end portion 12*d* of the endoscope 12.

The distal end portion 12*d* of the endoscope 12 is provided with an illumination optical system 30*a* and an image capture optical system 30*b*. The illumination optical system 30*a* includes an illumination lens 42, and the observation target is irradiated with illumination light propagated by the light guide 41 via the illumination lens 42. The image capture optical system 30*b* includes an objective lens 43, a zoom lens 44, and an image capture sensor 45. Various kinds of light, such as reflected light, scattered light, and fluorescence, from the observation target are incident on the image capture sensor 45 via the objective lens 43 and the zoom lens 44. As a result, an image of the observation target is formed on the image capture sensor 45. The zoom lens 44 freely moves between the telephoto end and the wide-angle end by operating the zoom operation portion 12*g*, thereby enlarging or reducing the observation target of which the image is formed on the image capture sensor 45.

The image capture sensor 45 is a color image capture sensor provided with any of a red (R) color filter, a green (G) color filter, or a blue (B) color filter for each pixel, and captures the image of the observation target and outputs image signals of respective RGB colors. A charge coupled device (CCD) image capture sensor or a complementary metal-oxide semiconductor (CMOS) image capture sensor can be used as the image capture sensor 45. Alternatively, a complementary color image capture sensor provided with complementary color filters, that is, cyan (C), magenta (M), yellow (Y), and green (G), may be used instead of the image capture sensor 45 provided with primary color filters. In a case where the complementary color image capture sensor is used, the image signals of four colors, that is, CMYG, are output. Therefore, the same RGB image signals as those of the image capture sensor 45 can be obtained by converting the image signals of the four colors, that is, CMYG, into the image signals of the three colors, that is, RGB, through the complementary color-primary color conversion. Alternatively, a monochrome image capture sensor that is not provided with color filters may be used instead of the image capture sensor 45.

A correlated double sampling/automatic gain control (CDS/AGC) circuit 46 performs correlated double sampling (CDS) or automatic gain control (AGC) on analog image signals that are obtained from the image capture sensor 45. The image signals that have been passed through the CDS/AGC circuit 46 are converted into digital image signals by an analog/digital (A/D) converter 47. The digital image signals after the A/D conversion are input to the processor device 16.

In the processor device 16, a program related to processing such as image storage processing is stored in a program memory (not shown). In the processor device 16, functions of an image acquisition unit 51, a noise reduction unit 53, a signal processing unit 55, an image storage unit 56, a display control unit 57, a video signal generation unit 58, a central control unit 59, and the like are realized by the program in the program memory being operated by the central control unit 59 composed of a processor. Further, the central control unit 59 receives information from the endoscope 12, such as the freeze operation portion 12*f*, and controls the endoscope 12 or the light source device 14 in addition to the control of each unit of the processor device 16, such as the image storage unit 56, based on the received information. Further, the central control unit 59 also receives information such as an instruction via the keyboard 19.

The image acquisition unit 51 acquires, for each frame, a digital image signal of an endoscope image obtained by imaging a subject, which is an observation target illuminated with illumination light, with the endoscope 12. "Frame" refers to a unit for controlling the image capture sensor 45 (see FIG. 2) that captures an image of the subject and, for example, "one frame" refers to a period including at least an exposure period in which the image capture sensor 45 is exposed to light from the observation target illuminated with illumination light and a read-out period in which an image signal is read out.

The acquired image signal is transmitted to a DSP 52. The DSP 52 performs digital signal processing, such as color correction processing, on the received image signal. The noise reduction unit 53 performs noise reduction processing by, for example, a moving average method or a median filtering method, on the image signal on which the color correction processing or the like has been performed by the DSP 52. The noise-reduced image signals are stored in the memory 54.

The signal processing unit 55 acquires the noise-reduced image signal from the memory 54. Then, signal processing, such as color conversion processing, color enhancement processing, and structure enhancement processing, is performed as necessary on the acquired image signal, and a color endoscope image in which the observation target appears is generated.

The image storage unit 56 performs image storage processing of storing images. The display control unit 57 controls display of an image or information on the display 18 serving as display means. For example, control to display the endoscope image on the display 18 in real time, control to display the stored still image in a set region, such as a sub screen of the display 18, or the like is performed.

The video signal generation unit 58 converts various endoscope images output from the display control unit 57 into video signals that can be displayed in full color on the display 18. The converted video signal is input to the display 18. As a result, the display 18 displays the endoscope image or various kinds of information in a text or the like.

Figure 5:
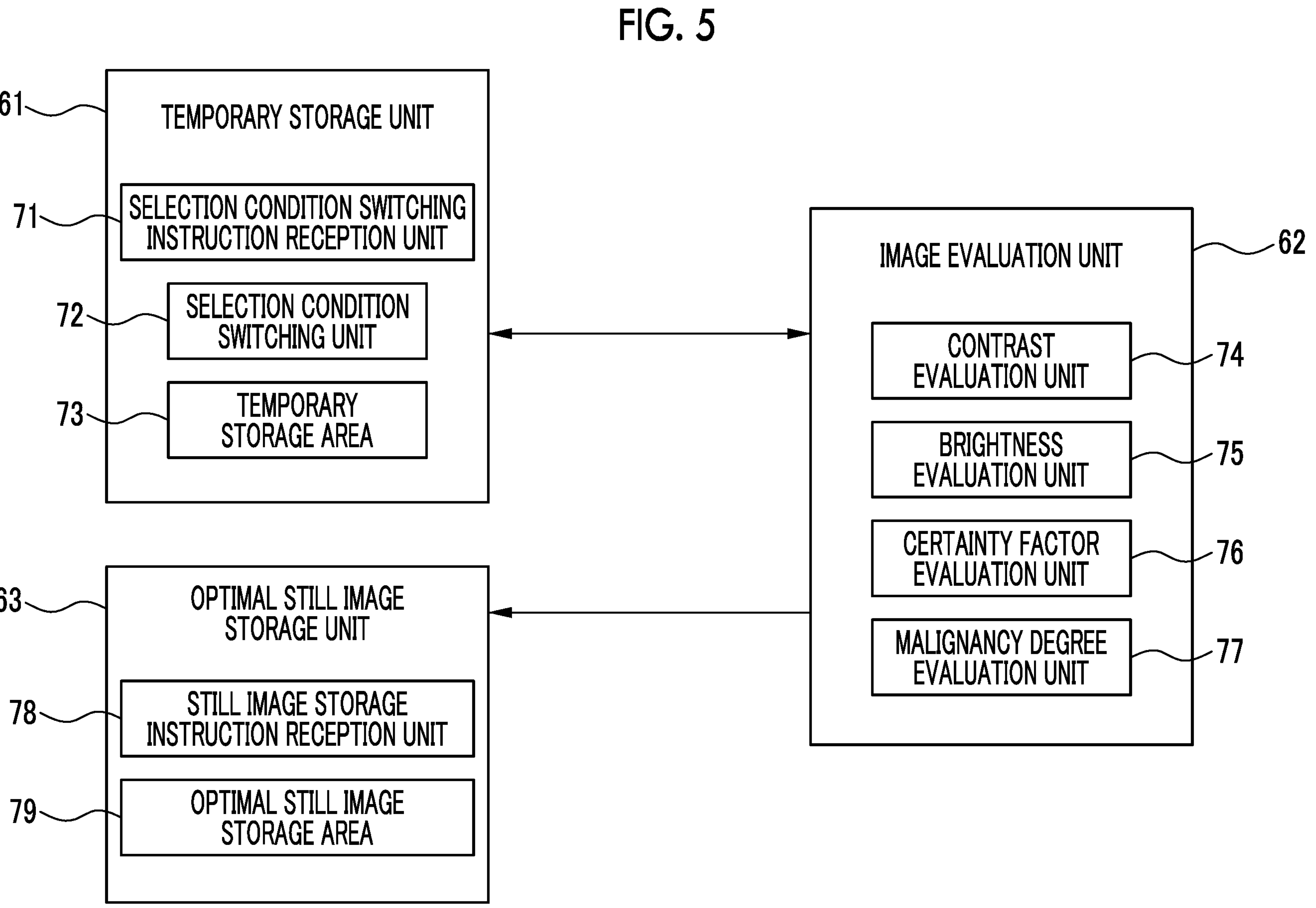
FIG. 5 is a block diagram showing a function of an image storage unit.

The image storage unit 56 comprises a temporary storage unit 61, an image evaluation unit 62, and an optimal still image storage unit 63. As shown in FIG. 5, the temporary storage unit 61 comprises a selection condition switching instruction reception unit 71, a selection condition switching unit 72, and a temporary storage area 73. The temporary storage unit 61 temporarily stores the endoscope image selected based on a selection condition in the temporary storage area 73 as a temporary storage image. The selection condition is a condition for selecting an endoscope image to be temporarily stored in the temporary storage area 73 with the endoscope image acquired for each frame by the image acquisition unit 51 as a target. The selection condition includes two kinds of a first selection condition and a second selection condition. The selection condition is switched by the selection condition switching unit 72 based on the selection condition switching instruction received by the selection condition switching instruction reception unit 71. The temporary storage area 73 has a function of a memory for temporarily storing the endoscope image and has a certain capacity.

The selection condition switching instruction reception unit 71 receives the selection condition switching instruction. The selection condition switching instruction is an instruction to switch the selection condition and is an instruction to switch the selection condition in a case where the temporary storage image selected from the endoscope images is temporarily stored in the temporary storage area 73 from the first selection condition to the second selection condition or from the second selection condition to the first selection condition. In a case where the selection condition switching instruction reception unit 71 receives the selection condition switching instruction, the selection condition switching unit 72 switches the selection condition. In a case where there is no selection condition switching instruction, the selection condition is not switched, and the previous selection condition is continued. The selection condition switching instruction and the still image storage instruction, which will be described below, are issued by an instruction unit. The selection condition switching instruction and the still image storage instruction issued by the instruction unit will be described below.

The image evaluation unit 62 performs image evaluation on each of the temporary storage images temporarily stored in the temporary storage area 73, thereby assigning an image evaluation value to each of the temporary storage images. The image evaluation unit 62 comprises a contrast evaluation unit 74, a brightness evaluation unit 75, a certainty factor evaluation unit 76, and a malignancy degree evaluation unit 77. The temporary storage image to which the image evaluation value is assigned is stored in the temporary storage area 73.

The image evaluation is an evaluation performed based on the temporary storage image, and examples thereof include a method of calculating an image evaluation value through image analysis for a feature amount of the temporary storage image or a method of assigning various values for the temporary storage image derived using a trained machine learning model as image evaluation values.

The image evaluation unit 62 performs image evaluation on contrast and/or brightness of the temporary storage image, and the image evaluation value can be a value related to contrast and/or brightness of the temporary storage image. Specifically, the contrast evaluation unit 74 performs image evaluation on contrast for each of the temporary storage images and assigns a contrast evaluation value to the corresponding temporary storage image. Further, the brightness evaluation unit 75 performs image evaluation on brightness for each of the temporary storage images and assigns a brightness evaluation value to the corresponding temporary storage image.

In addition, the image evaluation unit 62 performs image evaluation on a certainty factor and/or a malignancy degree related to a specific disease or the like for a lesion of the subject appearing in the temporary storage image, and the image evaluation value can be the certainty factor and/or the malignancy degree of the disease, or a value related thereto. Specifically, the certainty factor evaluation unit 76 performs image evaluation on the certainty factor related to the specific disease for each of the temporary storage images and assigns a certainty factor evaluation value to the corresponding temporary storage image. In addition, the malignancy degree evaluation unit 77 performs image evaluation on the malignancy degree related to the specific disease for each of the temporary storage images and assigns a malignancy degree evaluation value to the corresponding temporary storage image.

The contrast evaluation unit 74, the brightness evaluation unit 75, the certainty factor evaluation unit 76, the malignancy degree evaluation unit 77, and the like provided in the image evaluation unit 62 can each perform image evaluation using a known method. The contrast evaluation value assigned to the temporary storage image by the contrast evaluation unit 74 can be said to indicate that the higher the value is, the better or sharper the image is in focus, and the lower the value is, the greater the blur or shake is or the worse or less sharp the image is in focus. Therefore, using the contrast evaluation value, it is possible to select the endoscope image with the highest in-focus degree of the focus among the temporary storage images. The same applies to the brightness evaluation unit 75, the certainty factor evaluation unit 76, and the malignancy degree evaluation unit 77, and for example, it can be said that the higher the brightness evaluation value by the brightness evaluation unit 75 is, the brighter the endoscope image is, and the lower the brightness evaluation value is, the darker the endoscope image is. Therefore, in a case where the optimal still image is selected from the temporary storage images, it is possible to select the temporary storage image having a brightness evaluation value within a certain range.

Similarly, it can be said that the higher the certainty factor evaluation value by the certainty factor evaluation unit 76 is, the higher certainty factor the endoscope image has for a specific disease or the like in a feature part of the subject, and it can be said that the higher the malignancy degree evaluation value by the malignancy degree evaluation unit 77 is, the higher the malignancy degree of the specific lesion or the like in the feature part of the subject is.

The image evaluation value is not limited to these examples. In addition, in particular, in a case where image evaluation is performed using a trained machine learning model, for example, two or more of contrast, brightness, certainty factor, malignancy degree, and the like may be combined for evaluation, and each of the image evaluation values may not be assigned as an individually calculated image evaluation value.

The optimal still image storage unit 63 comprises a still image storage instruction reception unit 78 and an optimal still image storage area 79. The optimal still image storage unit 63 stores, based on the still image storage instruction received by the still image storage instruction reception unit 78, the optimal still image selected in accordance with the image evaluation value from the temporary storage images in the optimal still image storage area 79.

The optimal still image is a still image that is appropriate as a still image to be stored, and is, for example, a still image having an appropriate focus, brightness, or the like or including a feature region, such as a lesion. The optimal still image is a still image selected as a still image having an optimum focus or the like based on the image evaluation value from among the temporary storage images temporarily stored in the temporary storage area 73.

The still image storage instruction reception unit 78 receives the still image storage instruction. The still image storage instruction is issued by the instruction unit.

The instruction unit issues the selection condition switching instruction and the still image storage instruction. Therefore, it is preferable that the instruction unit performs a first operation and a second operation. The first operation and the second operation are different operations by the instruction unit. By the first operation and the second operation, different instructions between the selection condition switching instruction and the still image storage instruction can be issued even in a case where the instruction unit is, for example, one switch.

The instruction unit is an operation part for performing an instruction operation. An instruction by an operation of the operation part is controlled by a control unit. Specifically, the operation part for performing the instruction operation can be the freeze operation portion **12*f* provided in the operation part 12*b* of the endoscope 12. The control unit that controls the instruction by the operation can be the central control unit 59**.

The freeze operation portion **12*f* is a freeze switch among various scope switches of the endoscope 12 that is also referred to as a scope. A user operates the freeze operation portion 12*f*, whereby the selection condition switching instruction and the still image storage instruction are issued. The instruction unit may be other than the freeze operation portion 12*f* and may be, for example, a footswitch (not shown) connected to the processor device 16, a remote switch (not shown), or various switches provided in the processor device 16**.

The freeze operation portion 12f may be a momentary type switch or an alternate type switch to perform the first operation and the second operation. In a case where the freeze operation portion 12f is a momentary type switch, the first operation can be pressing of the momentary type switch, and the second operation can be releasing of the pressed momentary type switch. Specifically, in a case where the freeze operation portion 12f is a freeze switch of a momentary type switch, the selection condition switching instruction is issued in a case where the user continues the first operation, which is pressing of the freeze switch, and it is determined to be a long press. Further, an operation in which the user stops pressing the freeze switch and releases the switch can be set as the second operation, and the still image storage instruction can be issued in a case where the pressing of the freeze switch is released.

A case where the freeze operation portion 12f is the alternate type switch is similar to the case of the momentary type switch, the first operation can be first pressing and releasing of the alternate type switch, and the second operation can be second pressing and releasing of the alternate type switch. Specifically, in a case where the freeze operation portion 12f is a freeze switch of the alternate type switch, a case where the user presses the freeze switch once to turn on the switch, the on state is continued, and it is determined to be a long press is set as the first operation, and the selection condition switching instruction is issued in a case where the long press, which is the first operation, is performed. Further, an operation in which the user presses the freeze switch for the second time to turn off the switch can be set as the second operation, and the still image storage instruction can be issued in a case where the user presses the freeze switch for the second time.

The determination of the long press can be as follows. The operation of the freeze operation portion 12f is transmitted to the central control unit 59 of the processor device 16. The central control unit 59 receives and determines the operation of the freeze operation portion 12f The freeze operation portion 12f cooperates with the central control unit 59, measures a period from the first operation to the second operation in a case where the freeze operation portion 12f is a momentary type switch, and issues the selection condition switching instruction to the selection condition switching instruction reception unit 71 when a determination period set in advance has elapsed from the first operation in a case where the period is equal to or longer than the determination period. Alternatively, in a case where the freeze operation portion 12f is the alternate type switch, the time from the first pressing and releasing, which is the first operation, is measured, and in a case where this time is equal to or longer than the determination period set in advance, the selection condition switching instruction is issued to the selection condition switching instruction reception unit 71 when the determination period has elapsed from the first operation.

Even in a case where the instruction unit is other than the freeze operation portion 12f, two kinds of instructions, that is, the selection condition switching instruction and the still image storage instruction, can be preferably issued by using a momentary type switch, an alternate type switch, or the like as the instruction unit.

Figure 6:
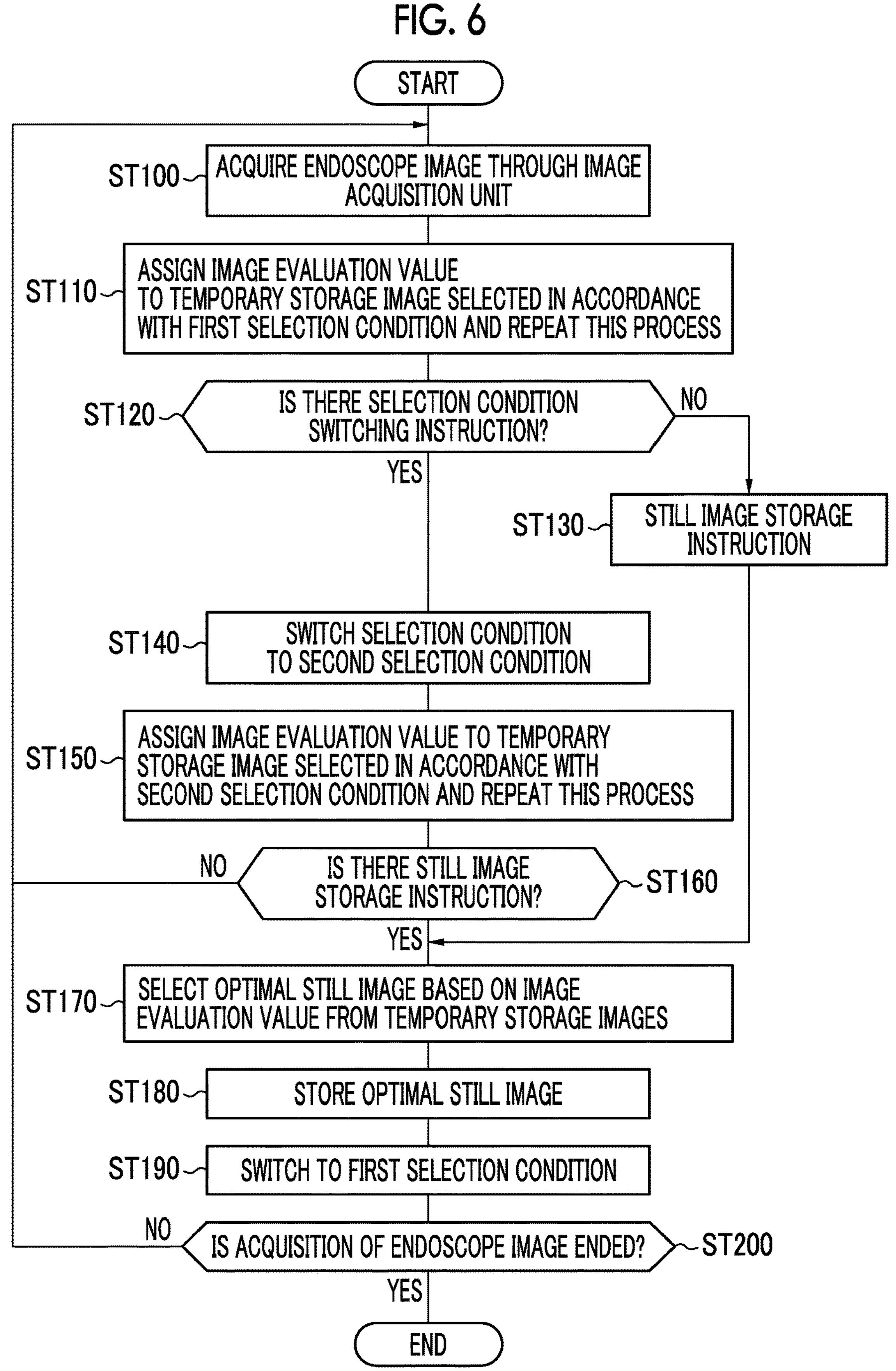
FIG. 6 is a flowchart showing a series of flows of storage of an optimal still image.

Next, the operation and the like of the endoscope system 10 will be described more specifically. As shown in FIG. 6, in the observation using the endoscope system 10, the user images the observation target as a subject with the endoscope 12 to obtain the endoscope image. The image acquisition unit 51 acquires the endoscope image for each frame (step ST100). The image acquisition unit 51 acquires the endoscope image in the order of the imaging time. Then, the image evaluation value is assigned to the temporary storage image selected in accordance with the first selection condition, and this process is repeated (step ST110).

It is preferable that the temporary storage unit 61 temporarily stores the endoscope image selected based on the first selection condition, in a case where the image acquisition unit 51 starts to acquire the endoscope image. In the first selection condition, the endoscope images may be temporarily stored in the temporary storage area 73 in the order of the imaging time by a first in first out (FIFO) method. It is preferable that the selected endoscope image is temporarily stored in the temporary storage area 73 in a number equal to or less than a maximum number set in advance as the temporary storage image.

The first selection condition can comprise a first A selection condition and a first B selection condition. In a case where the temporary storage image is temporarily stored in the temporary storage area 73 in a number less than the maximum number, the first A selection condition is used. In the first A selection condition, the endoscope images are temporarily stored in the temporary storage area 73 as the temporary storage images in the order of the most recent imaging time until the maximum number is reached. In a case where the maximum number of temporary storage images are temporarily stored in the temporary storage area 73, the first B selection condition is used. In the first B selection condition, the temporary storage image with the oldest imaging time, among the temporary storage images temporarily stored in the temporary storage area 73, is deleted from the temporary storage area, and then the endoscope images are temporarily stored in the temporary storage area 73 as the temporary storage images in the order of the most recent imaging time, and these processes are repeatedly performed. As described above, by employing the first in first out method in the first B selection condition, the number of temporary storage images to be temporarily stored in the temporary storage area 73 can be prevented from exceeding the maximum number set in advance.

Figure 7:
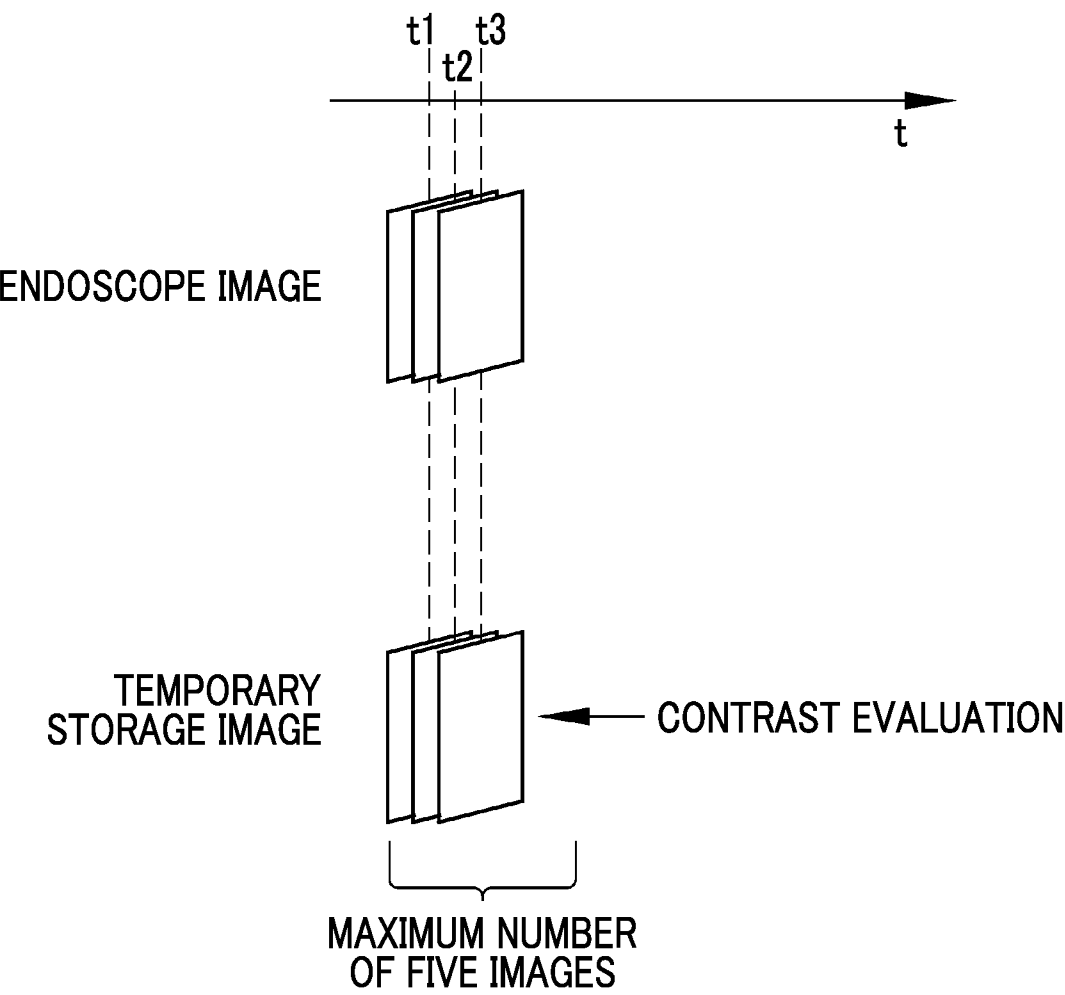
FIG. 7 is an explanatory diagram illustrating a first A selection condition.

As shown in FIG. 7, for example, the maximum number of images is set to five, and the first A selection condition is used in a case where the temporary storage image is temporarily stored in the temporary storage area 73 in a number less than five. In the first A selection condition, since the temporary storage image is temporarily stored in the temporary storage area 73 in a number less than five, the endoscope images are temporarily stored in the temporary storage area 73 in the order of the most recent imaging time until the number of temporary storage images reaches the maximum number of five. Therefore, in a case where the capturing of the endoscope image is started at time t1, the endoscope image captured at time t1 to the endoscope image captured at time t3 are temporarily stored in the temporary storage area 73 at time t3. Subsequently, the temporary storage images are temporarily stored in the temporary storage area 73 in the order in which the endoscope images are acquired until the number of temporary storage images reaches the maximum number of five.

Figure 8:
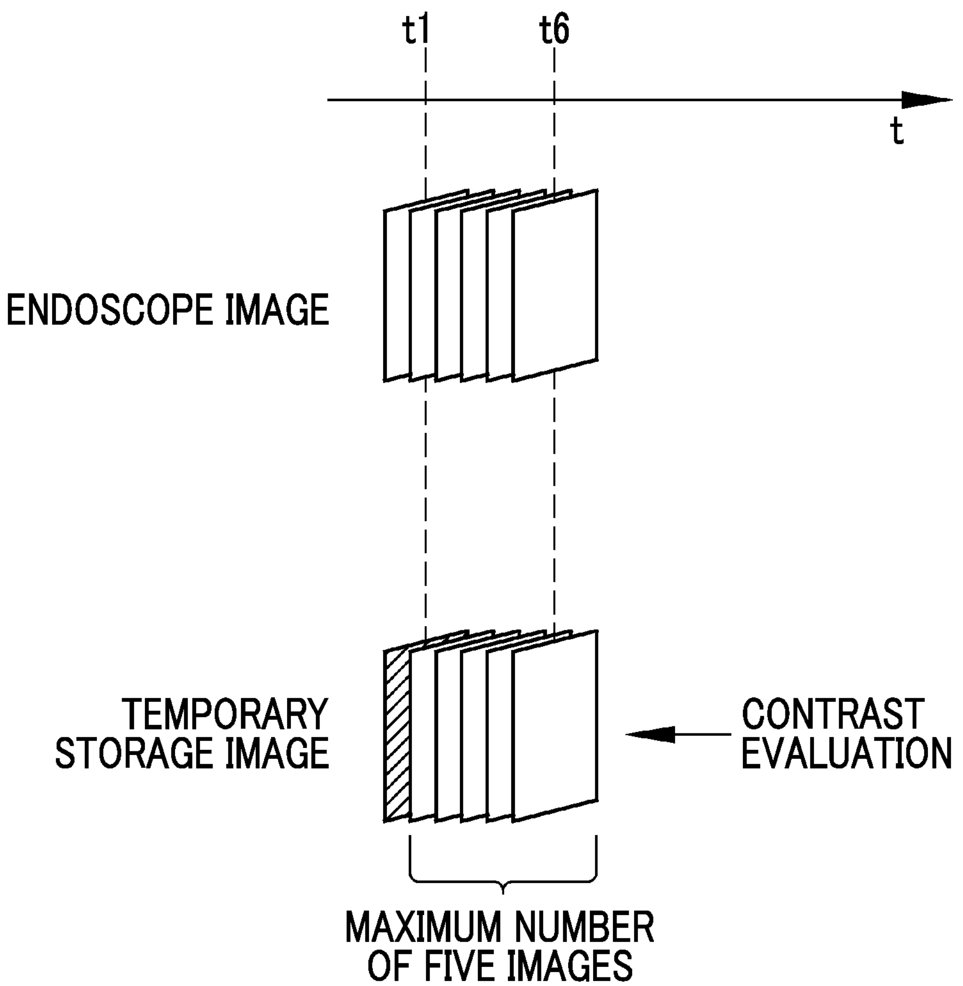
FIG. 8 is an explanatory diagram illustrating a first B selection condition.

As shown in FIG. 8, in a case where five temporary storage images, that is, the maximum number of images, are temporarily stored in the temporary storage area 73, the first B selection condition is used. In the first B selection condition, since the maximum number of temporary storage images are temporarily stored in the temporary storage area 73, the number of temporary storage images not exceeding the maximum number of images are always temporarily stored in the temporary storage area 73 by the first in first out method. Therefore, in a case where the endoscope image is acquired at time t6, the endoscope image captured at time t1 is deleted from the temporary storage area 73, and then the endoscope image captured at latest time t6 is temporarily stored in the temporary storage area 73. In FIG. 8, the image to be deleted is indicated by hatching. In this way, since the number of temporary storage images stored in the temporary storage area 73 does not become larger than the maximum number set in advance, it is possible to prevent an increase in memory capacity.

An image evaluation value is assigned by the image evaluation unit 62 to each of the temporary storage images temporarily stored in the temporary storage area 73. In the present embodiment, the contrast evaluation unit 74 evaluates contrast for each of the temporary storage images and assigns the contrast evaluation value to the corresponding temporary storage image. It can be said that the higher the contrast evaluation value is, the better the endoscope image is in focus, and the lower the contrast evaluation value is, the greater the blur, shake, or the like is and the more the endoscope image is out of focus.

Next, in a case where the selection condition switching instruction is issued (YES in step ST120), the selection condition is switched to the second selection condition (step ST140). The selection condition switching instruction is issued by the instruction unit as described above. In the present embodiment, the instruction unit includes the freeze operation portion 12*f* of the endoscope 12, and the selection condition switching instruction is issued in a case where the long press of the freeze operation portion 12*f* is performed. A case where the selection condition switching instruction is not issued (NO in step ST120) will be described below. After switching the selection condition to the second selection condition, the image evaluation value is assigned to the temporary storage image selected in accordance with the second selection condition, and this process is repeated (step ST150).

The second selection condition can comprise a second A selection condition and a second B selection condition. The second A selection condition is the same as the first A selection condition. In a case where the temporary storage image is temporarily stored in the temporary storage area 73 in a number less than the maximum number, the second A selection condition is used. In the second A selection condition, the endoscope images are temporarily stored in the temporary storage area 73 as the temporary storage images in the order of the most recent imaging time until the maximum number is reached. In a case where the maximum number of temporary storage images are temporarily stored in the temporary storage area 73, the second B selection condition is used. In the second B selection condition, only a proper still image selected in accordance with the contrast evaluation value from the temporary storage image is left in the temporary storage area as the temporary storage image, the images other than the proper image are deleted from the temporary storage area, and then, the second A selection condition is performed again. The proper still image is a still image selected as a candidate for selecting the optimal still image. As described above, in the second B selection condition, by using a method of repeating a flow of leaving, among the maximum number of temporary storage images, for example, one proper still image based on the contrast evaluation value, deleting the other temporary storage images, adding the temporary storage images in the order of the imaging time again, and leaving one proper still image based on the contrast evaluation value again in a case where the number of temporary storage images has reached the maximum number, it is possible to prevent the number of temporary storage images to be temporarily stored in the temporary storage area 73 from exceeding the maximum number set in advance.

Figure 9:
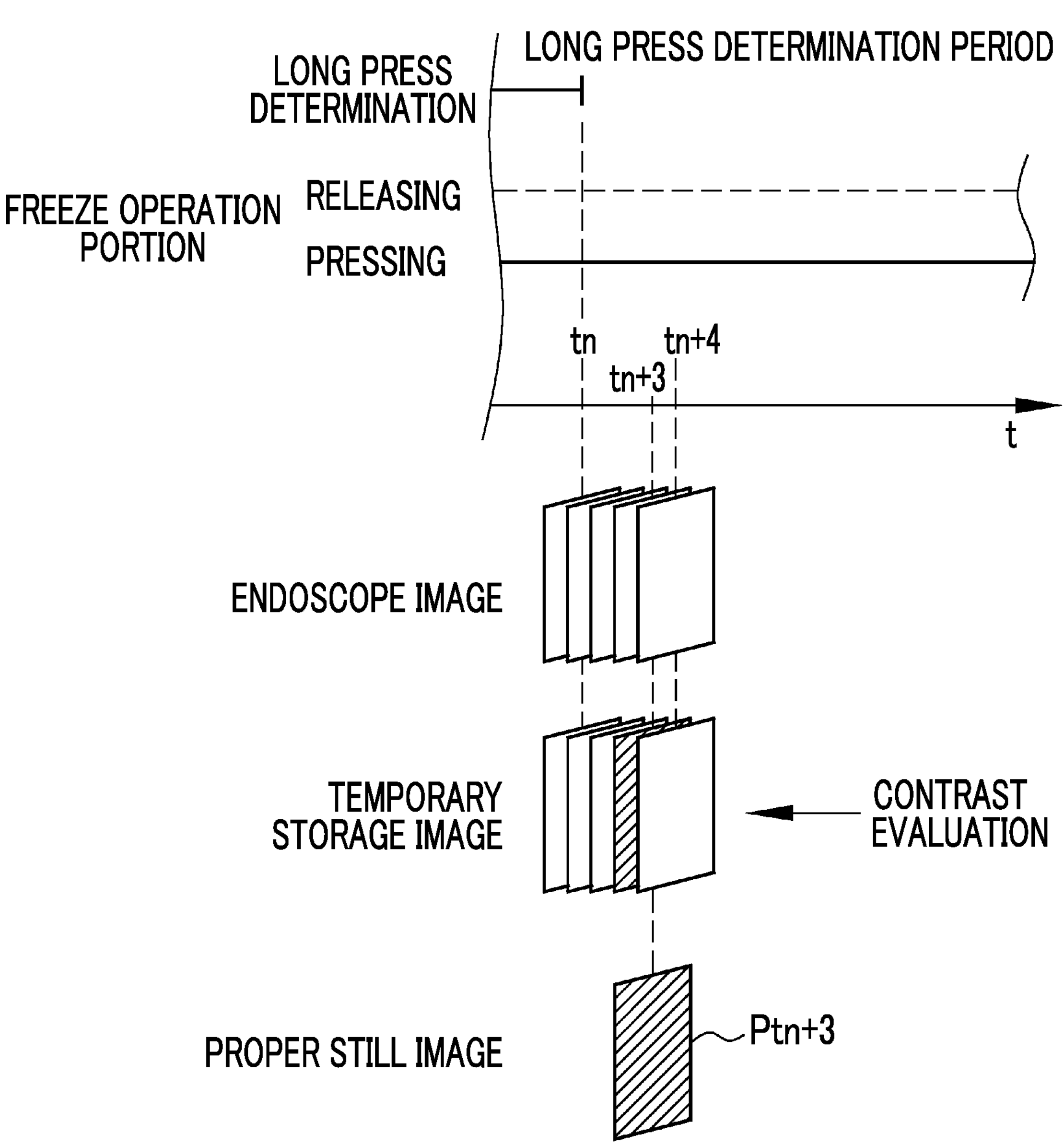
FIG. 9 is an explanatory diagram illustrating a first half part of a second B selection condition and of a second C selection condition.

As shown in FIG. 9, in a case where it is determined as the long press because the period of the pressing of the freeze operation portion 12*f* exceeds a long press determination period at time tn, the selection condition switching instruction is issued at time tn and the selection condition switching unit 72 switches the selection condition from the first selection condition to the second selection condition. In the second selection condition, in a case where five temporary storage images, that is, the maximum number of images, are temporarily stored in the temporary storage area 73, the second B selection condition is used. Whether the second A selection condition or the second B selection condition is used in a case where it is determined as the long press is decided depending on how many temporary storage images are stored in the temporary storage area 73 when it is determined as the long press. In the second B selection condition, in the first half, in a case where the endoscope images captured from time tn to time tn+4 are set as the temporary storage images, one endoscope image Ptn+3, which is the temporary storage image having the highest contrast evaluation value, is selected as the proper still image from these temporary storage images. In FIG. 9, the endoscope image Ptn+3, which is selected from the temporary storage images and is the proper still image, is indicated by hatching. Among the temporary storage images, temporary storage images other than the proper still image are deleted from the temporary storage area 73.

Figure 10:
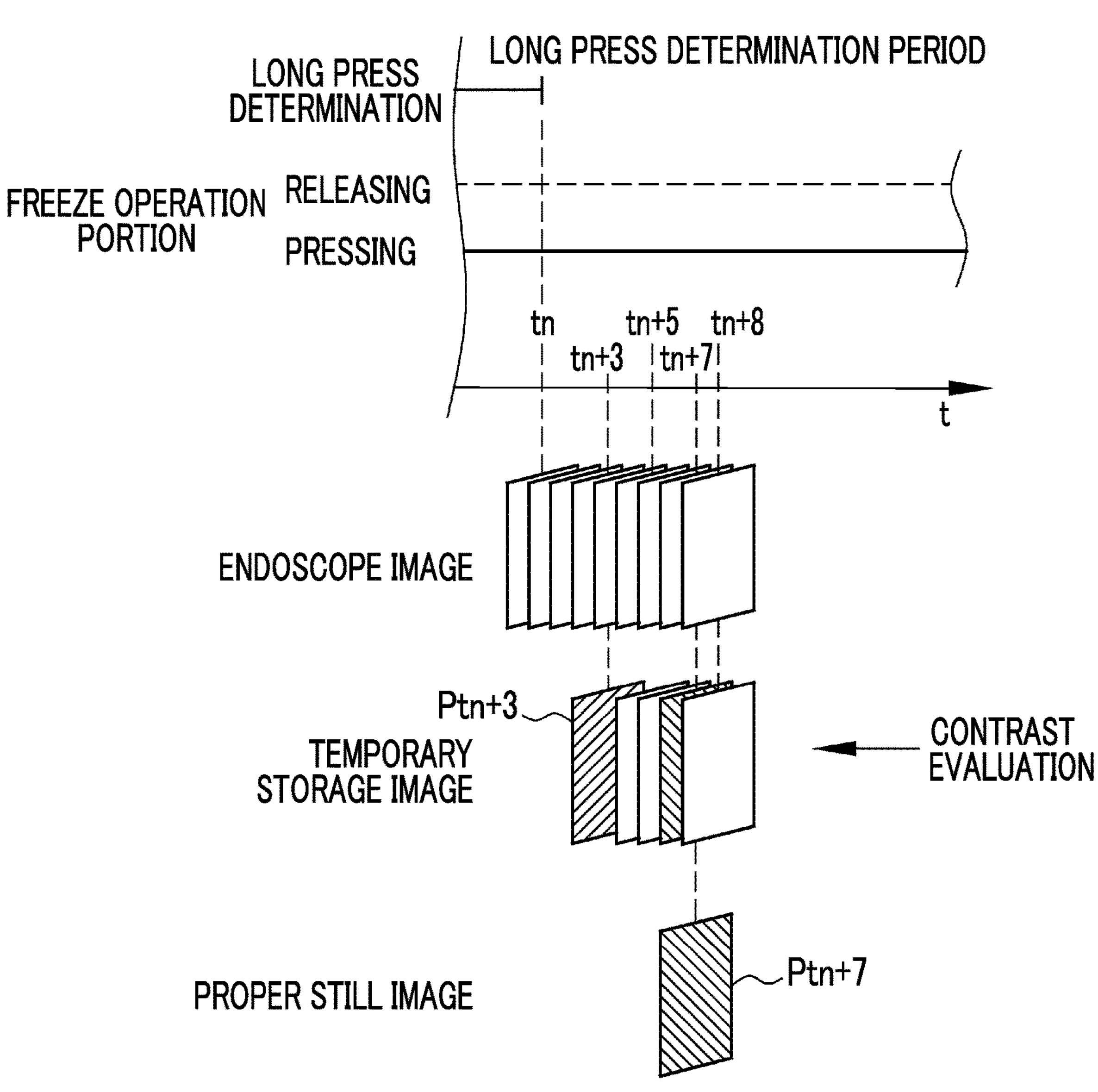
FIG. 10 is an explanatory diagram illustrating a second half part of the second B selection condition.

Next, as shown in FIG. 10, in the second half of the second B selection condition, in a state in which the endoscope image Ptn+3, which is the proper still image captured at time tn+3, is temporarily stored in the temporary storage area 73 as the temporary storage image, endoscope images captured from time tn+5 to time tn+8, which are the next imaging timings, are temporarily stored in the temporary storage area 73 as temporary storage images. At a point in time when five temporary storage images, which are the maximum number of images, are temporarily stored in the temporary storage area 73, the second B selection condition is performed. That is, the proper still image is selected based on the contrast evaluation value from the five temporary storage images, which are the maximum number of images, temporarily stored in the temporary storage area 73, and, in the case of FIG. 10, one endoscope image Ptn+7 captured at time tn+7 is selected as the proper still image. In FIG. 10, the endoscope image Ptn+3 that has been the proper still image and the endoscope image Ptn+7 that is newly obtained as the proper still image are indicated by hatching different from each other. The update of the proper still image is continued during the long press of the freeze operation portion 12*f*. In this way, since the proper still image is temporarily stored while being updated, it is possible to acquire a more appropriate still image. In addition, since the number of temporary storage images to be stored in the temporary storage area 73 does not become larger than the maximum number set in advance, it is possible to prevent an increase in memory capacity.

The second selection condition can comprise the second A selection condition and a second C selection condition. First, in a case where the temporary storage images are temporarily stored in the temporary storage area 73 in a number less than the maximum number, the second A selection condition is used. In a case where the maximum number of temporary storage images are temporarily stored in the temporary storage area 73, the second C selection condition is used. In the second C selection condition, in a case where the maximum number of temporary storage images are temporarily stored in the temporary storage area, only the proper still image selected in accordance with the contrast evaluation value from the temporary storage images is temporarily stored in the temporary storage area as the temporary storage image, and then an endoscope image with the most recent imaging time is selected and temporarily stored in the temporary storage area as the temporary storage image. After that only the proper still image selected in accordance with the contrast evaluation value from the temporary storage images temporarily stored in the temporary storage area is temporarily stored in the temporary storage area as the temporary storage image. After that, the second C selection condition is repeated. As described above, in the second C selection condition, by using a method of repeating a flow of leaving, among the maximum number of temporary storage images, for example, one proper still image in the temporary storage area based on the contrast evaluation value, adding one temporary storage image in the order of the imaging time again, and then, comparing the contrast evaluation values of the two temporary storage images with each other to leave one proper still image, and adding one temporary storage image in the order of the imaging time again, it is possible to prevent the number of temporary storage images to be temporarily stored in the temporary storage area 73 from exceeding the maximum number set in advance.

In the second selection condition, in a case where five temporary storage images, that is, the maximum number of images, are temporarily stored in the temporary storage area 73, the second C selection condition may be used. In the second C selection condition, in the first half, as shown in FIG. 9, in a case where five endoscope images, that is, the maximum number of images, captured from time tn to time tn+4 are set as the temporary storage images, one temporary storage image having the best contrast evaluation value is selected as the proper still image from these temporary storage images. Among these temporary storage images, the temporary storage images other than the endoscope image Ptn+3, which is the proper still image, are deleted from the temporary storage area 73.

Figure 11:
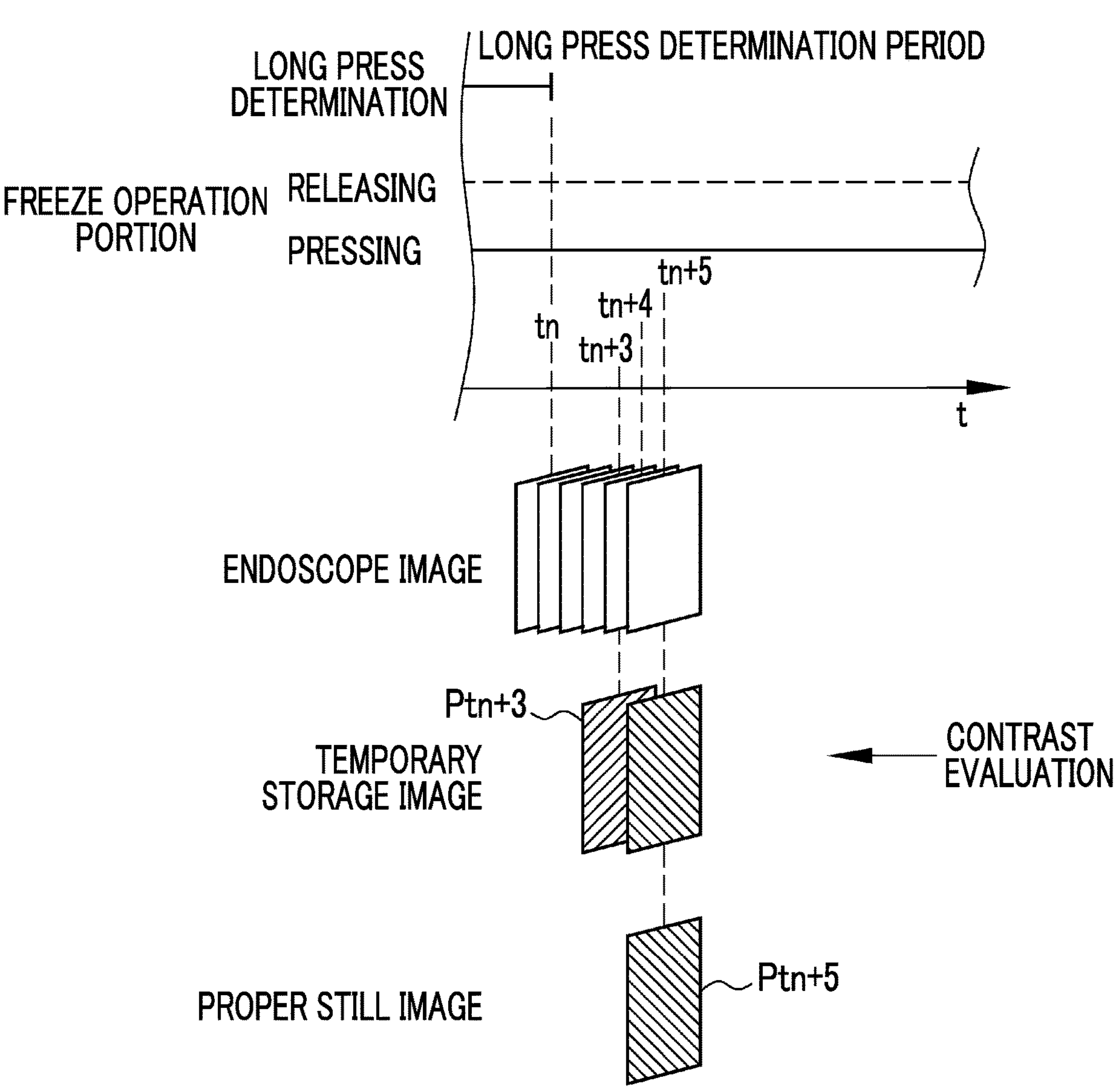
FIG. 11 is an explanatory diagram illustrating a second half part of the second C selection condition.

Next, as shown in FIG. 11, in the second half of the second C selection condition, after time tn+4, in a state in which the proper still image captured at time tn+3 is temporarily stored in the temporary storage area as the temporary storage image, the endoscope image captured at time tn+5, which is the next imaging timing, is temporarily stored in the temporary storage area 73 as temporary storage image. After the two temporary storage images of the endoscope image Ptn+3, which is the proper still image captured at time tn+3, and the endoscope image Ptn+5 captured at time tn+5 are temporarily stored in the temporary storage area, the contrast evaluation values of the two temporary storage images are compared with each other, thereby leaving one endoscope image Ptn+5 captured at time tn+5, which has a higher contrast evaluation value, as a new proper still image. In FIG. 11, the endoscope image Ptn+3 that has been the proper still image and the endoscope image Ptn+5 that is newly obtained as the proper still image are indicated by hatching different from each other. A flow is repeated in which the endoscope image captured at time tn+6 (not shown), which is the next imaging timing, is temporarily stored in the temporary storage area 73 as the temporary storage image in a state in which the proper still image captured at time tn+5 is temporarily stored in the temporary storage area, the proper still image captured at time tn+5 and two temporary storage images captured at time tn+5 and time tn+6 are temporarily stored in the temporary storage area, and then the contrast evaluation values of the two temporary storage images are compared with each other. In this way, since the proper still image is temporarily stored while being updated, it is possible to acquire a more appropriate still image. In addition, since the number of temporary storage images to be stored in the temporary storage area 73 does not become larger than the maximum number set in advance, it is possible to prevent an increase in memory capacity.

Next, in a case where the still image storage instruction is issued (YES in step ST160), the optimal still image is selected from the temporary storage images based on the image evaluation value (step ST170). The optimal still image is a still image that is appropriate as a still image to be stored. The still image storage instruction is issued by the instruction unit as described above. In the present embodiment, since the instruction unit includes the freeze operation portion **12*f* of the endoscope 12, the still image storage instruction is issued in a case where the pressing of the freeze operation portion 12*f***, which is the second operation, is released.

As described above, the still image storage instruction is issued by the second operation of the freeze operation portion **12*f* In the present embodiment, an operation in which the user releases the pressing of the freeze switch, which is the freeze operation portion 12*f***, can be set as the second operation, and the still image storage instruction can be issued in a case where the pressing of the freeze switch is released.

Figure 12:
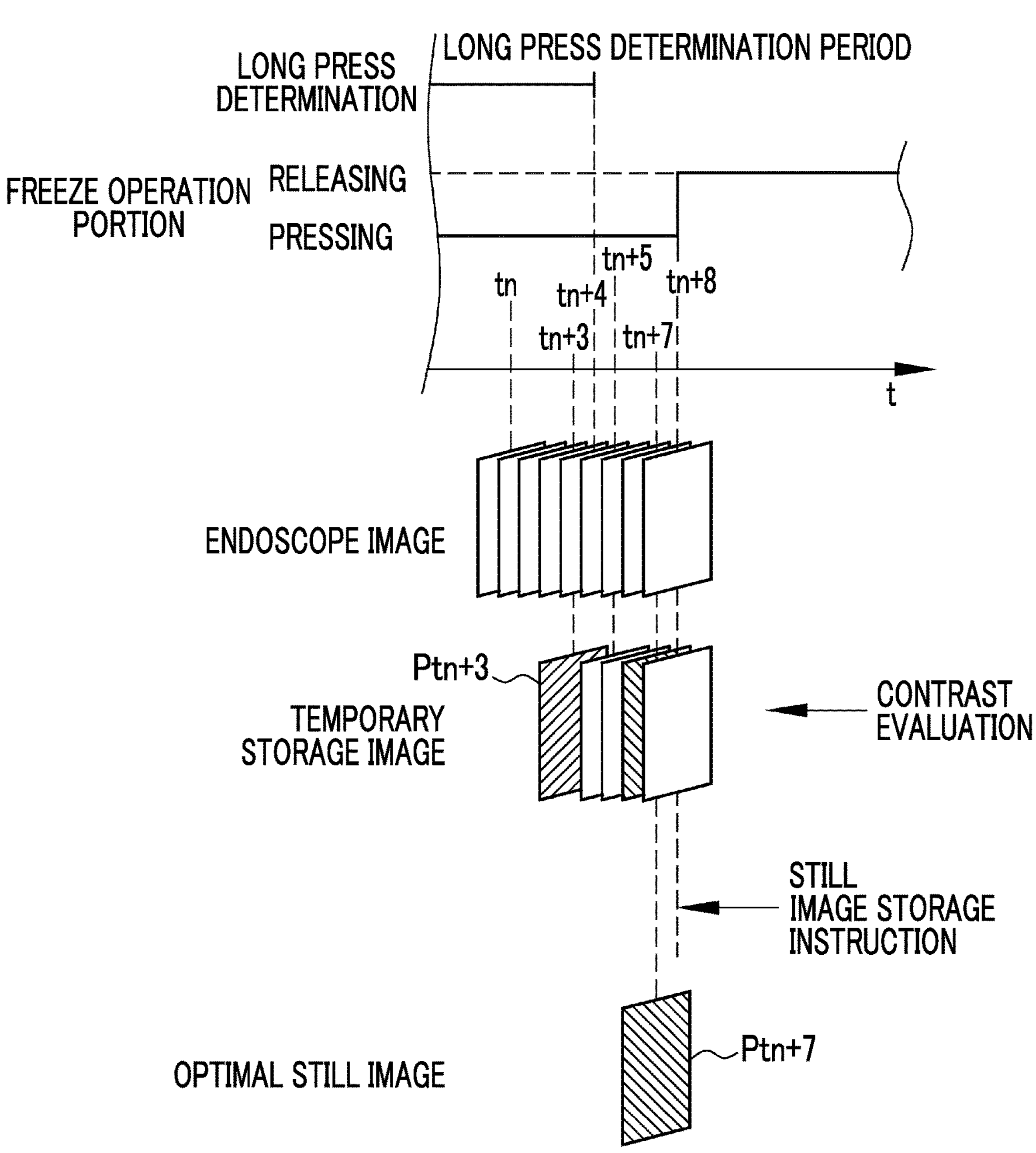
FIG. 12 is an explanatory diagram illustrating a still image storage instruction issued in the second B selection condition.

As shown in FIG. 12, in a case where the endoscope images are temporarily stored under the second B selection condition, there are five temporary storage images temporarily stored in the temporary storage area 73 in a case where the pressing of the freeze operation portion **12*f* is released by the still image storage instruction and the still image storage instruction is issued. Therefore, one optimal still image is selected from among the five temporary storage images based on the contrast evaluation value. The five temporary storage images include the endoscope image Ptn+3 captured at time tn+3 and the endoscope image Ptn+7 captured at time tn+7. The endoscope image captured at time tn+3 is a past proper still image that is an endoscope image having the highest contrast evaluation value among the five endoscope images captured from time tn to time tn+4. In FIG. 12, the endoscope image Ptn+3 that has been the proper still image and the endoscope image Ptn+7 that is newly obtained as the proper still image are indicated by hatching different from each other. In a case where the endoscope image Ptn+7 is selected by comparing the endoscope image Ptn+3 with the endoscope image Ptn+7 in accordance with the contrast evaluation value, the endoscope image Ptn+7 that is the most in-focus endoscope image among the 10** endoscope images captured from time tn to time tn+9 is selected as the optimal still image.

Figure 13:
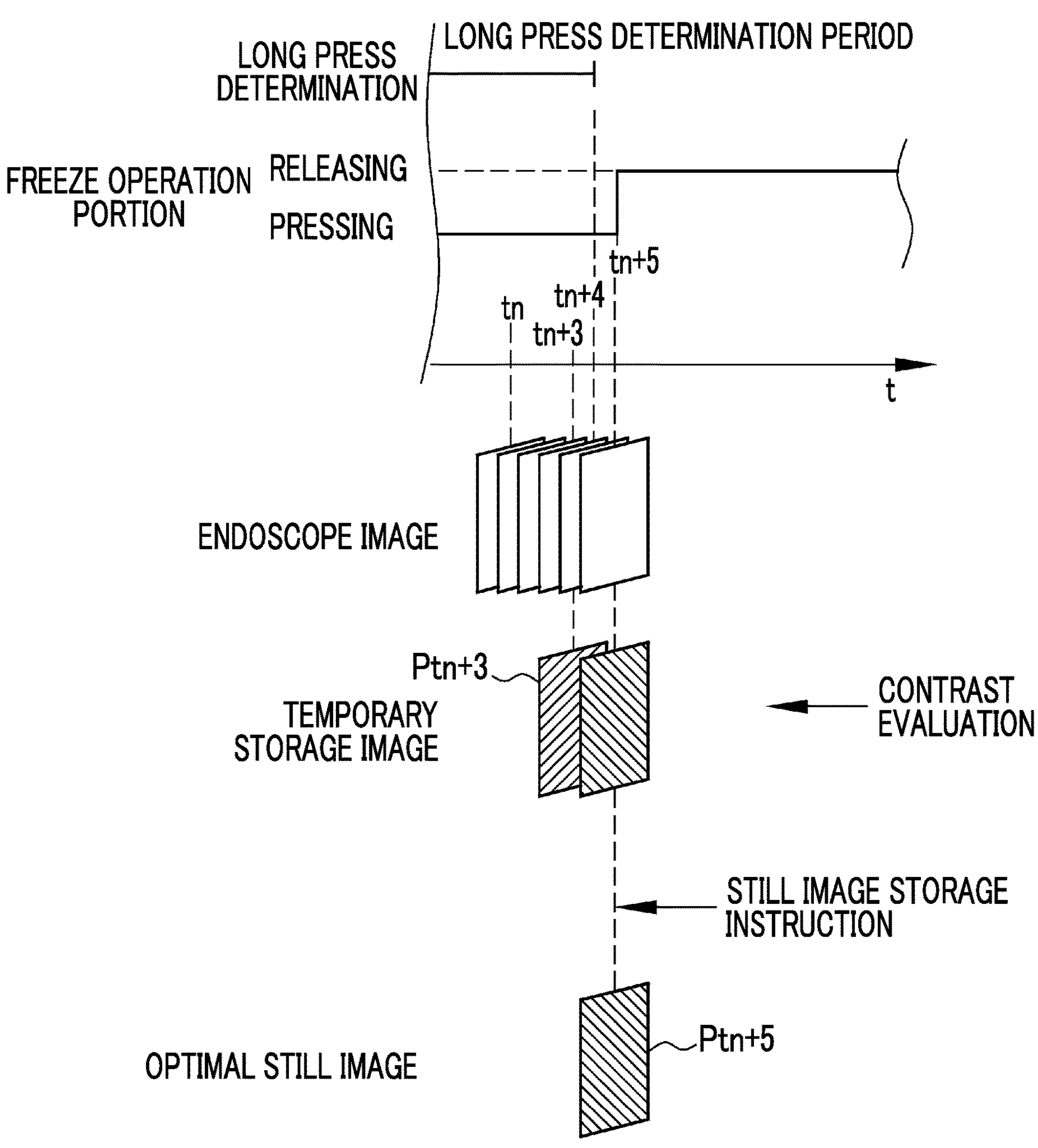
FIG. 13 is an explanatory diagram illustrating the still image storage instruction issued in the second C selection condition.

Similarly, as shown in FIG. 13, in a case where the endoscope images are temporarily stored under the second C selection condition, there are five temporary storage images temporarily stored in the temporary storage area 73 in a case where the pressing of the freeze operation portion **12*f* is released and the still image storage instruction is issued. Therefore, one optimal still image is selected from among the five temporary storage images based on the contrast evaluation value. The five temporary storage images are endoscope images captured from time tn to time tn+4 and include the endoscope image Ptn+3 captured at time tn+3. The endoscope image Ptn+3 is a past proper still image that is an endoscope image having the highest contrast evaluation value among the five endoscope images captured from time tn to time tn+4. In a case where the endoscope image Ptn+5 is selected by comparing the endoscope image Ptn+3 with the endoscope image Ptn+5 acquired by the image acquisition unit 51 after the still image storage instruction in accordance with the contrast evaluation value, the endoscope image Ptn+5 that is the most in-focus endoscope image among the six endoscope images captured from time tn to time tn+5 is selected as the optimal still image. In FIG. 13**, the endoscope image Ptn+3 that has been the proper still image and the endoscope image Ptn+5 acquired after the still image storage instruction are indicated by hatching different from each other.

The optimal still image selected as described above is stored in the optimal still image storage area 79 (step ST180). The optimal still image stored in the optimal still image storage area 79 is a still image having an excellent image evaluation value. In the present embodiment, since the contrast evaluation value is used as the image evaluation value, the optimal still image is an excellent in-focus endoscope image. Therefore, the optimal still image is suitable to be displayed on the display 18 or to be used for a medical report.

Next, the selection condition is switched from the second selection condition to the first selection condition (step ST190). In a case where the temporary storage unit temporarily stores the endoscope image based on the second selection condition after the optimal still image is stored, the central control unit 59 issues the selection condition switching instruction to the selection condition switching instruction reception unit 71. In a case where the acquisition of the endoscope image is ended (YES in step ST200), the observation by the endoscope is ended. In a case where the acquisition of the endoscope image is not ended (NO in step ST200), the process returns to step ST100, and the process is repeated from the temporary storage of the endoscope image under the first selection condition.

A case where the selection condition switching instruction is not issued in step ST120 (NO in step ST120) is a case where the pressing of the freeze operation portion **12*f* is not determined as the long press, and is a case where the pressing of the freeze operation portion 12*f* is determined as the single press in which the duration of the pressing is less than the long press determination time. In this case, since the pressing of the freeze operation portion 12*f* is released, the still image storage instruction is issued (step ST130), and the process proceeds to step ST170 where the optimal still image is selected. In step ST170 in a case where the single press of the freeze operation portion 12*f*** is performed, the optimal still image is selected with the temporary storage image selected in accordance with the first selection condition as a target.

As described above, the endoscope system 10 can more reliably acquire the optimum still image at a timing intended by the user through an easy operation by the user, such as a single press or a long press of the freeze switch, for example. Even in a case where it is considered that the optimum still image cannot be obtained immediately after the freeze switch is pressed because of changes in imaging environment, such as variations in the distance between the distal end portion **12*d* of the endoscope and the observation target as a subject, it is possible to obtain the optimum still image through an easy operation of continuously pressing the freeze switch and continuing the long press until the optimum still image is obtained and of releasing the freeze switch in a case where it is considered that the optimum still image is obtained. Further, simply by bringing the endoscope distal end portion 12*d* as close as possible to the observation target and gradually moving away while pressing the freeze switch, it is possible to obtain, for example, the optimum still image that is in focus. Conversely, simply by gradually approaching the observation target while pressing the freeze switch from a point in time when the distance between the endoscope distal end portion 12*d*** and the observation target is far, it is possible to obtain, for example, the optimum still image that is in focus. Further, in this case, since the temporary storage images are temporarily stored in a number set in advance, it is possible to suppress an increase in capacity of a memory for the temporary storage images.

Figure 14:
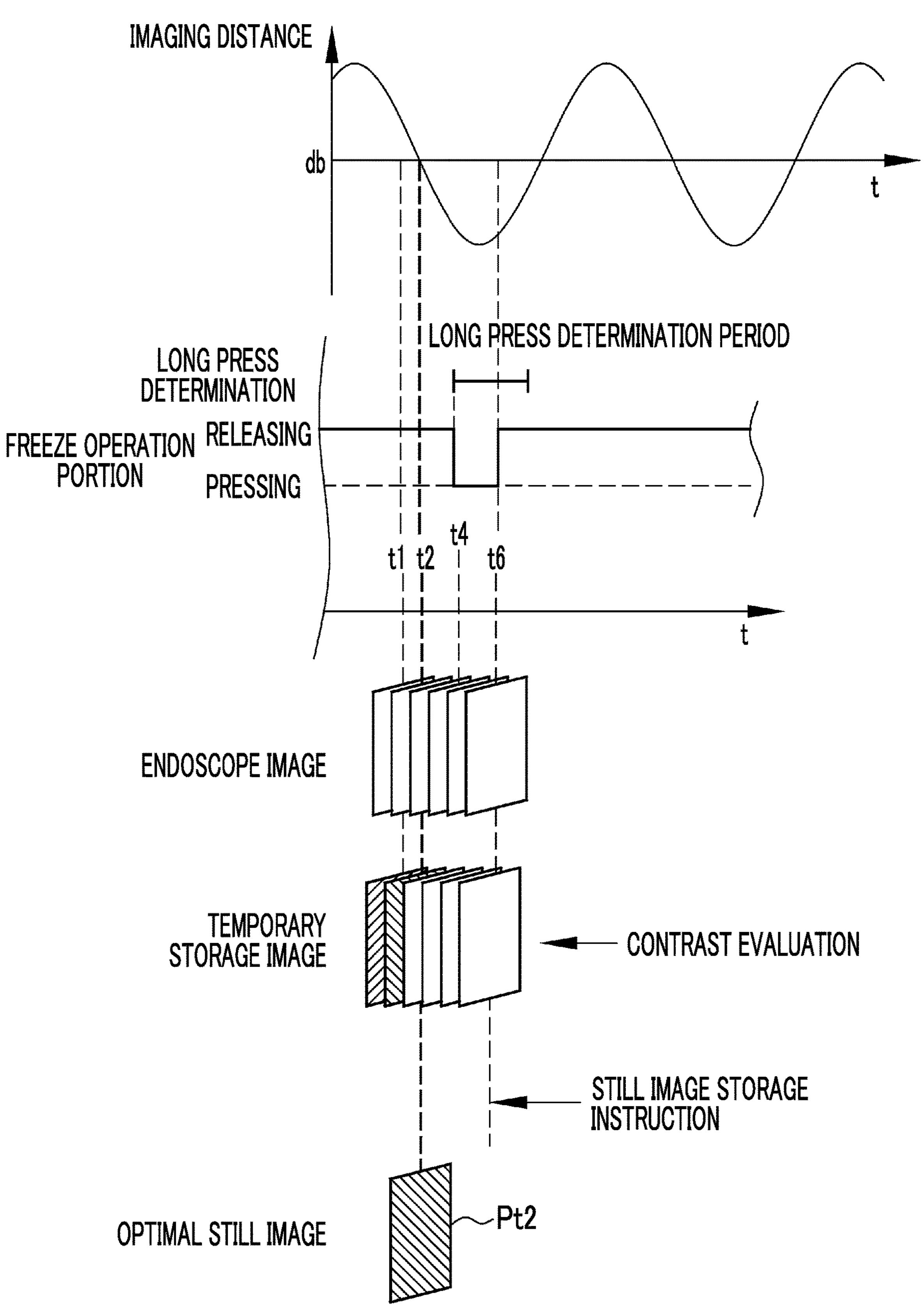
FIG. 14 is an explanatory diagram illustrating acquisition of the optimal still image by a single press of a freeze switch.
Figure 15:
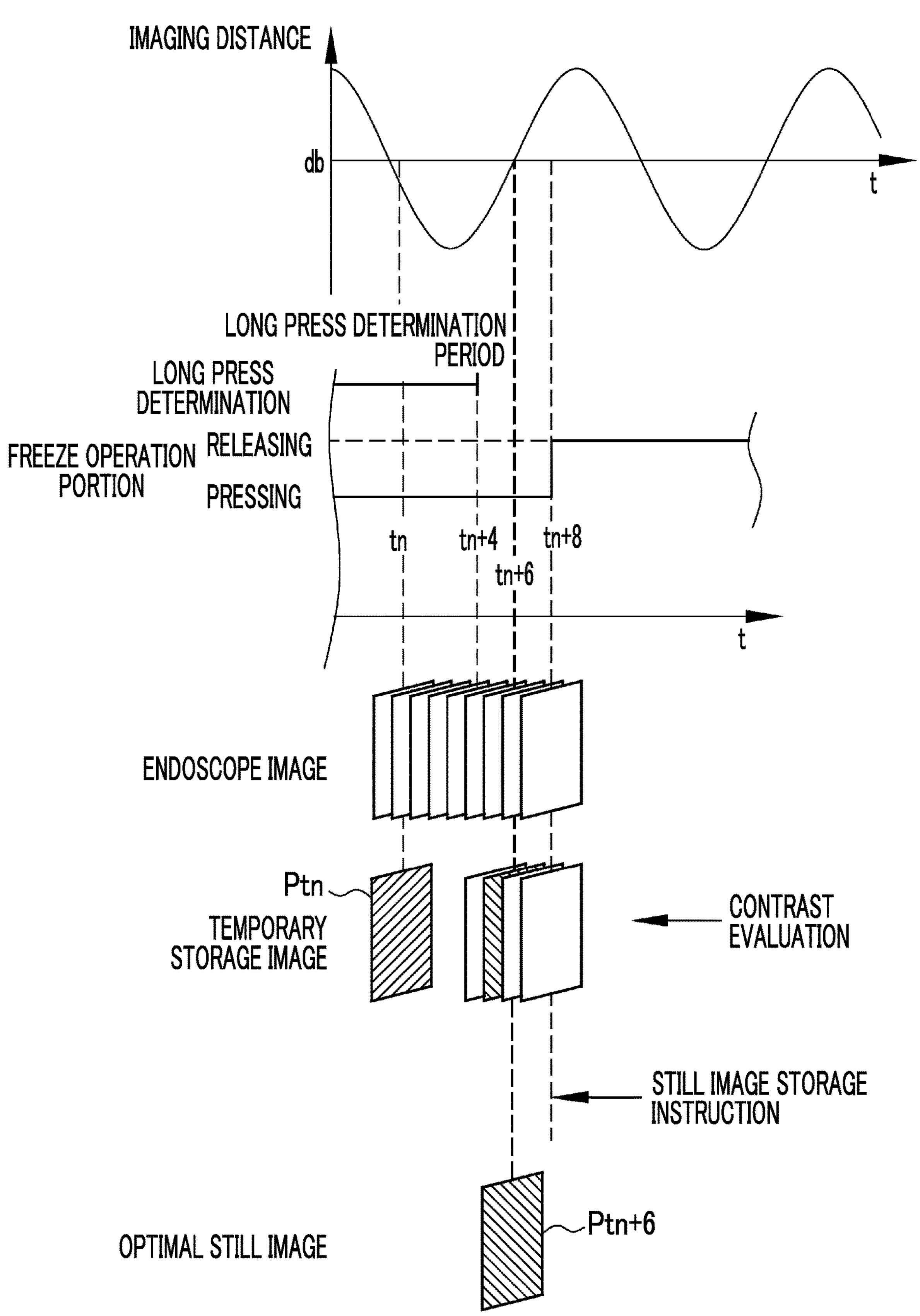
FIG. 15 is an explanatory diagram illustrating acquisition of the optimal still image by a long press of the freeze switch.
Figure 20:
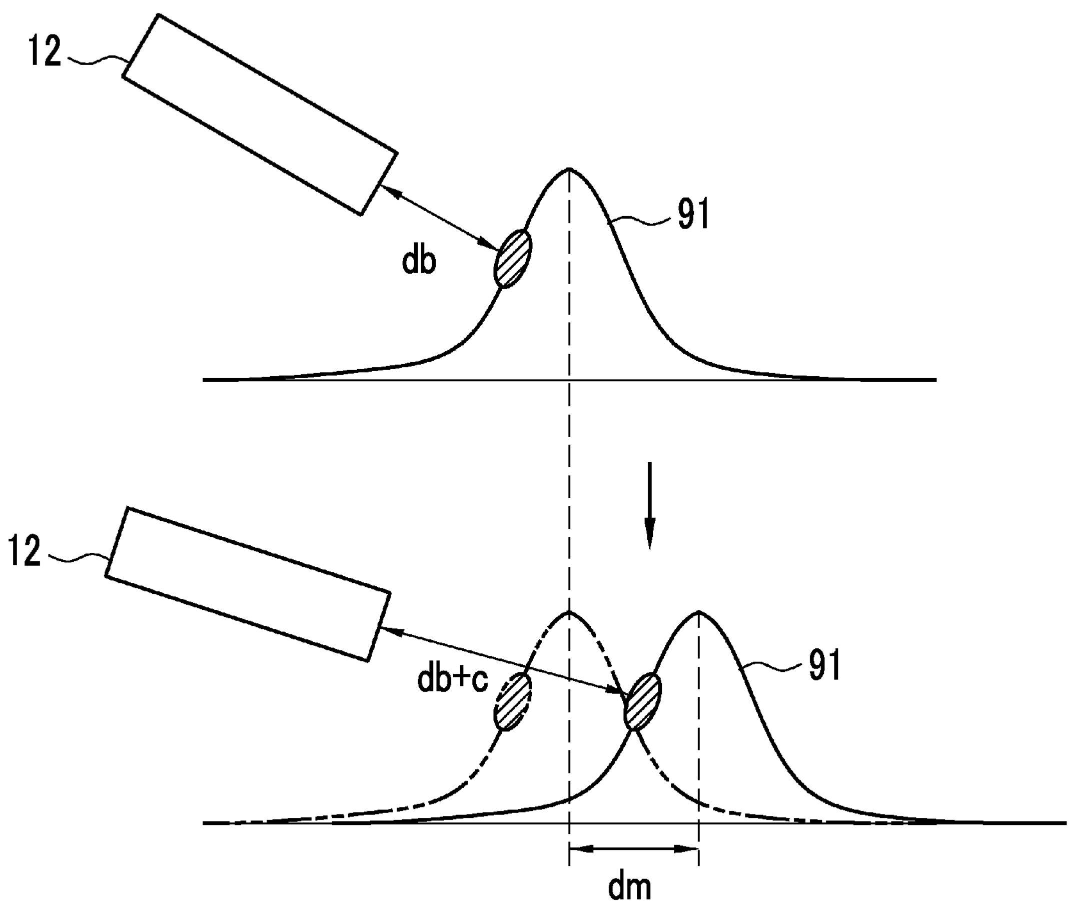
FIG. 20 is an explanatory diagram illustrating a case where a focus of an endoscope image varies.

As shown in FIGS. 14 and 15, since the endoscope system 10 switches the selection condition between the first selection condition and the second selection condition, even in a case where the most in-focus endoscope image is not obtained when the freeze operation portion **12*f* is pressed, an optimal still image with the most excellent focus can be easily and reliably obtained by performing the long press in which the pressing of the freeze operation portion 12*f* is continued until a point in time when it is considered that the most in-focus endoscope image is obtained. In the graphs shown in the upper part of FIGS. 14 and 15, the vertical axis represents the imaging distance, and the horizontal axis represents time t. Further, the imaging distance is a distance between the distal end portion 12*d* of the endoscope and the subject and is based on a distance db in the graph. The distance db is a distance at which the most excellent in-focus image is obtained (see FIG. 20). Since the subject is the observation target of the endoscope 12 and is located inside the lumen of a subject to be examined, the imaging distance may regularly vary with time t due to pulsation, peristalsis, or the like, for example, even in a case where the position of the distal end portion 12*d* of the endoscope 12** is fixed.

In a case where the user tries to acquire the still image, the temporary storage image is temporarily stored under the first selection condition in a case where the period from the pressing to the releasing of the freeze operation portion **12*f* is shorter than the long press determination period. In the case of FIG. 14, the temporary storage images are temporarily stored in the temporary storage area 73 with the maximum number of five images. Since the first selection condition is the first in first out method, five images are obtained as the temporary storage images by going back from time t6 at which the freeze operation portion 12*f* is released, and an endoscope image Pt2 acquired at time t2 and having the highest contrast evaluation value from among them is acquired as the optimal still image. In FIG. 14, the endoscope image that is acquired at time t1 and that is deleted in a case where the endoscope image acquired at time t6 becomes the temporary storage image, and the endoscope image acquired at time t2** are indicated by hatching different from each other.

The case of FIG. 14 is a case where an excellent in-focus endoscope image is obtained in a period in which the maximum number of images are acquired. However, an excellent endoscope image may not be obtained in a period in which the maximum number of images are acquired, depending on the timing of the single press of the freeze operation portion **12*f*. That is, there may be a case where the timing to obtain the endoscope image with an imaging distance of the distance db is not included within a certain period that goes back from a point in time of the single press of the freeze operation portion 12***f* In the endoscope system 10, as shown in FIG. 15, for example, in a case where it is considered that an excellent endoscope image is not obtained in a period in which the maximum number of images are acquired by the single press, the user need only continue to press the freeze operation portion 12*f* In a case where the period from the pressing to the releasing of the freeze operation portion 12*f* is longer than the long press determination period, it is determined as the long press, and the first selection condition is changed to the second selection condition, and then the temporary storage image is stored. In the endoscope system 10, by displaying the optimal still image on the display 18, it is possible to confirm whether or not the appropriate still image is obtained by the single press of the freeze operation portion 12*f* Displaying the optimal still image will be described below.

In the case of FIG. 15, the long press determination is performed at time tn+4, and after the long press determination, the endoscope image is temporarily stored in the temporary storage area 73 under the second selection condition. In the second selection condition, the temporary storage images are temporarily stored in the temporary storage area 73 with the maximum number of five images. Four endoscope images from time tn+5 to time tn+8 are temporarily stored as the temporary storage images in a state in which only an endoscope image Ptn that is the temporary storage image acquired at time tn and having the highest contrast evaluation value under the first selection condition before the long press determination is temporarily stored in the temporary storage area 73. At time tn+8 at which the five temporary storage images are temporarily stored in the temporary storage area 73, the contrast evaluation is performed on the five temporary storage images temporarily stored in the temporary storage area 73 in accordance with the contrast evaluation values, and an endoscope image Ptn+6 having the highest contrast evaluation value is stored as the optimal still image. In FIG. 15, the endoscope image Ptn that is the proper still image and is acquired at time tn, and the endoscope image Ptn+6 acquired at time t6 are indicated by different hatching. In this way, the endoscope image Ptn is updated, and a more excellent in-focus endoscope image Ptn+6 can be stored as the optimal still image.

In this way, for example, the user continues to press the freeze operation portion 12*f* until the user considers that the timing to obtain the optimum imaging distance is included, and releases the freeze operation portion 12*f* in a case where the user considers that the timing to obtain the optimum imaging distance is included, whereby it is possible to acquire the still image with the most appropriate imaging distance even in a case where the subject moves.

In the present embodiment, a case where the maximum number of temporary storage images to be temporarily stored in the temporary storage area 73 is five has been described, but the maximum number of images can be arbitrarily set according to an imaging purpose, an imaging environment, or the like. For example, in a case where the number of frames is 60 per second, the maximum number of images can be 15. The maximum number of 15 images corresponds to an imaging period of 0.25 seconds in a case where the number of frames is 60 images/second.

Further, the maximum number of temporary storage images to be temporarily stored in the temporary storage area 73 may not be endoscope images of consecutive frames. The imaging period corresponding to the maximum number of images may be arbitrarily set, and endoscope images of non-consecutive frames may be temporarily stored as temporary storage images. For example, in a case where the number of frames is 60 frames/second, acquiring the maximum number of 15 images from consecutive frames corresponds to an imaging period of 0.25 seconds, but acquiring the maximum number of 15 images every other frame corresponds to an imaging period of 0.5 seconds. The imaging period corresponding to the maximum number of images can be referred to as a blur reduction period, for example, in a case where the image evaluation value is set as the contrast evaluation value. The blur reduction period is a period in which at least one proper still image that is optimum with regard to the image evaluation value can be acquired even in a case where the image evaluation value varies during this period. Therefore, any adjustment can be made according to the type of the subject, the imaging environment, or the like, such as setting the blur reduction period to be short in a case of a quickly moving subject and setting the blur reduction period to be long in a case of a slowly moving subject, for example.

Further, the maximum number of temporary storage images to be temporarily stored in the temporary storage area 73 or the imaging period may be adjusted by the first operation and the second operation of the instruction unit. Specifically, in a case where the long press period of the freeze operation portion 12*f* is equal to or shorter than a determination period set in advance, the imaging period corresponding to the maximum number of images can be set to 0.25 seconds in a case where the number of frames is 60 images/second, and the imaging period can be set to 0.5 seconds by acquiring the maximum number of 15 images for every other frame in a case where the long press period is longer than the determination period. The determination period for the imaging period determination based on the long press period may be set in three or more stages instead of only two stages as described above.

Figure 16:
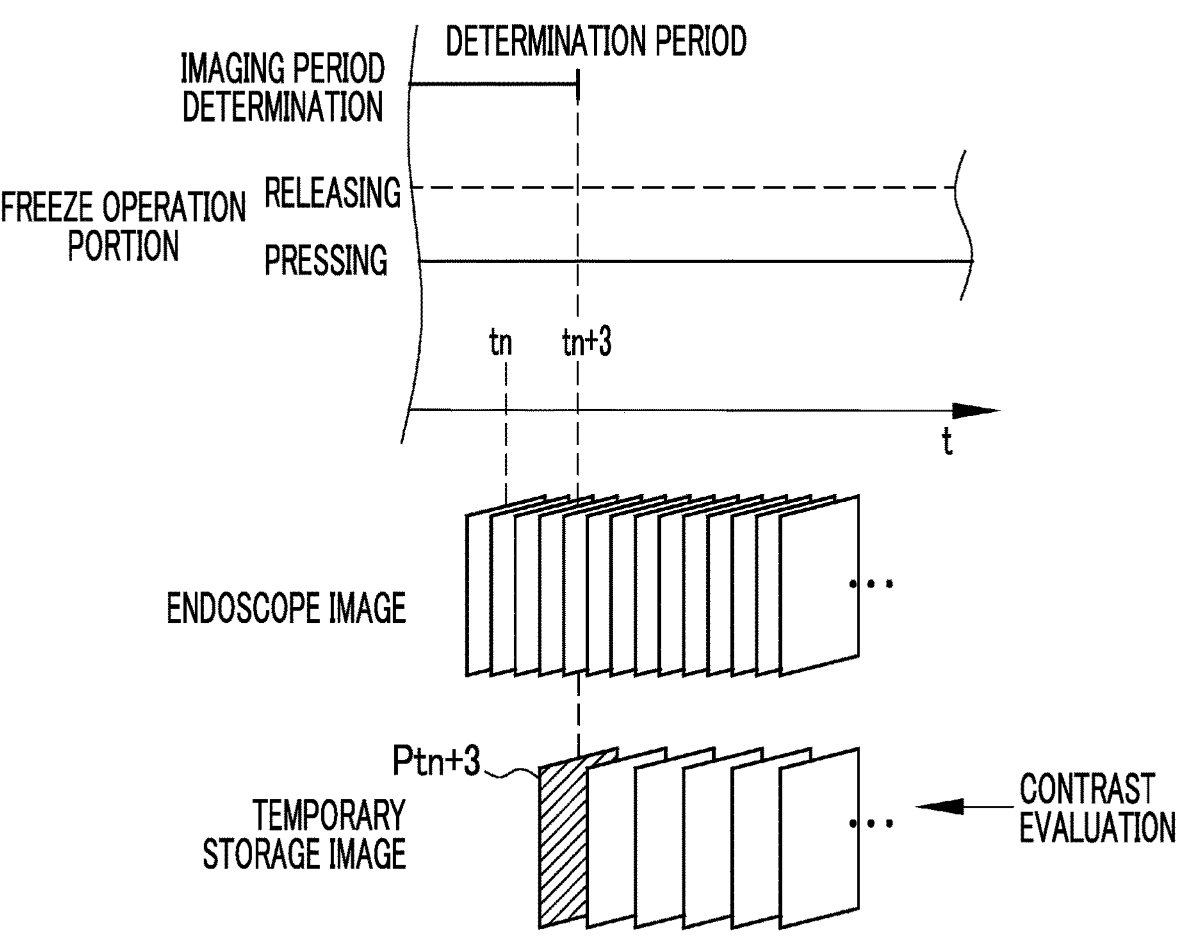
FIG. 16 is an explanatory diagram regarding a temporary storage image to be acquired every other frame.

As shown in FIG. 16, in the imaging period determination based on the long press period, in a case where the determination period has elapsed at time tn+3, the temporary storage unit 61 selects and temporarily stores the temporary storage images not for each frame of the endoscope image but every other frame. Further, this selection condition may be included in the second selection condition. In the case of FIG. 16, the maximum number of images is 15. Therefore, at a point in time when the number of temporary storage images including the endoscope image Ptn+3 captured at time tn+3 becomes 15, the optimal still image is selected from among the 15 temporary storage images based on the contrast evaluation value and is stored. Accordingly, the long press period is relatively long, and the period to acquire the maximum number of images is set long in a case where the user is carefully observing the observation target, so that the timing to update the optimal still image can also be set long. As described above, the instruction unit can adjust the period to acquire the maximum number of images.

Alternatively, in a case where the image evaluation unit 62 sets a threshold value for the image evaluation value and assigns the image evaluation value equal to or greater than the threshold value to the temporary storage image, the optimal still image storage unit 63 may consider that the still image storage instruction is issued and may store the temporary storage image to which the image evaluation value equal to or greater than the threshold value is assigned as the optimal still image. That is, a threshold value may be set for the image evaluation value in advance, and in a case where a temporary storage image having an image evaluation value equal to or greater than the threshold value is acquired, this temporary storage image may be stored as the optimal still image, regardless of whether or not there is a still image storage instruction. As a result, in a case where the optimal still image is displayed on the display, the user can release the long press after recognizing that the optimal still image is stored through the display 18 or the like while continuing the long press.

Figure 17:
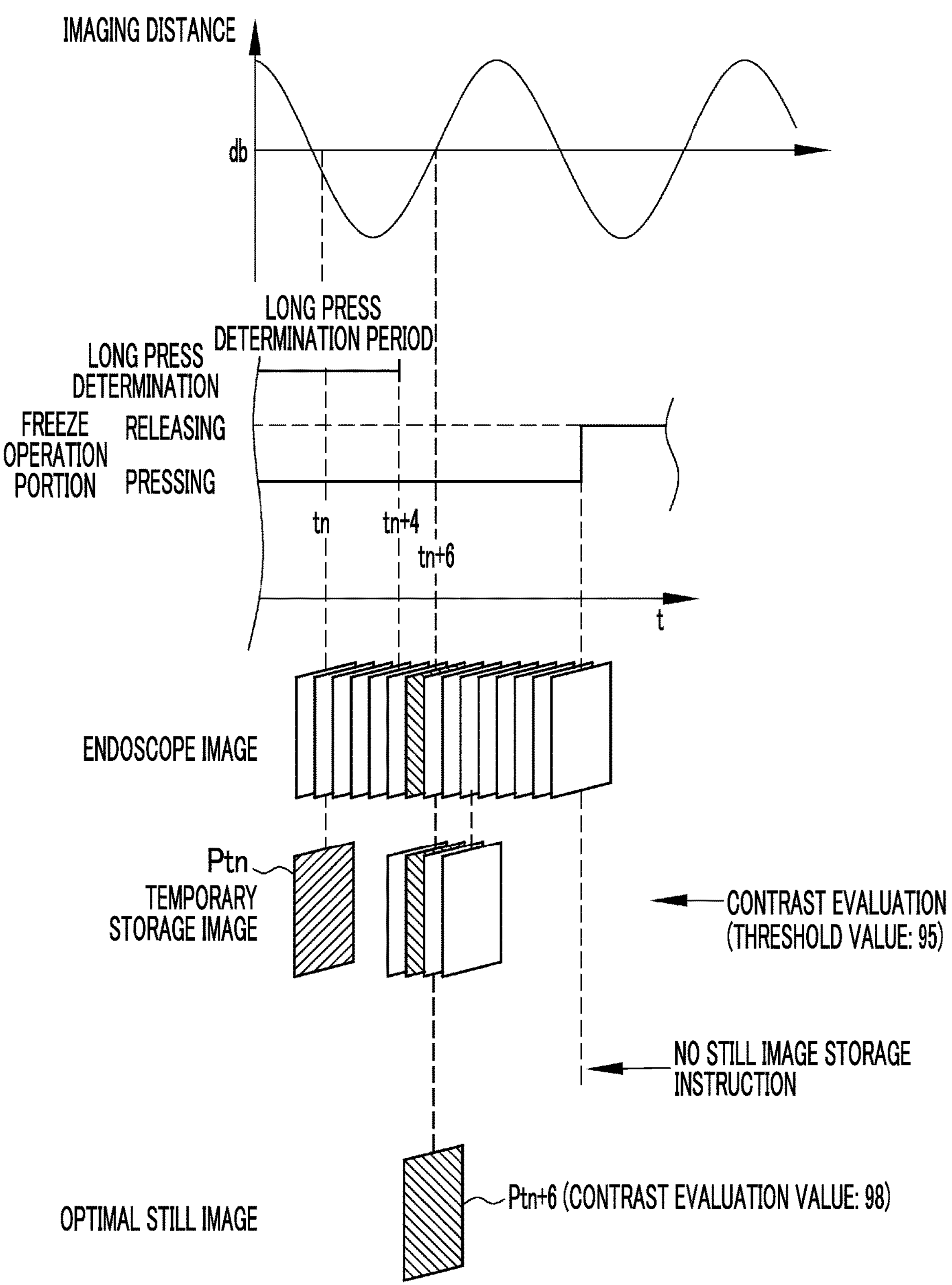
FIG. 17 is an explanatory diagram illustrating a case where a threshold value of an image evaluation value is used.

As shown in FIG. 17, the threshold value of the contrast evaluation value is set to 95. The contrast evaluation value can be set as a relative value in a case where the contrast evaluation value of the image in focus with almost no blur is set to 100. In a case where the temporary storage image Ptn+6 having a contrast evaluation value of 98 is temporarily stored among the temporary storage images during the long press, the temporary storage unit 61 stores the temporary storage image Ptn+6 as the optimal still image. In a case where the temporary storage image equal to or greater than the threshold value is acquired after time Ptn+6, the new temporary storage image may be stored as the optimal still image or may not be stored. The user knows that the optimal still image has been acquired by the notification from the notification unit. Specifically, for example, the user can know that the optimal still image has been acquired by a notification such as the optimal still image being displayed on the display 18 or an alert or the like being displayed on the display 18. The user can confirm whether or not the target still image has been acquired on the display 18 or the like, and can end the long press in a case where the target still image has been acquired. The notification unit will be described below.

The display 18 may display the stored optimal still image and/or proper still image. In a case where the display 18 displays the optimal still image and/or the proper still image, the display 18 can update the optimal still image and/or the proper still image to display the latest optimal still image and/or the latest proper still image. In addition, the display 18 may comprise a main screen and a sub screen. The optimal still image may be displayed on the main screen for a certain period and may be displayed on the sub screen after the certain period. Further, the optimal still image and the proper still image may be displayed on the main screen and the sub screen by being updated to the latest images, respectively.

Figure 18:
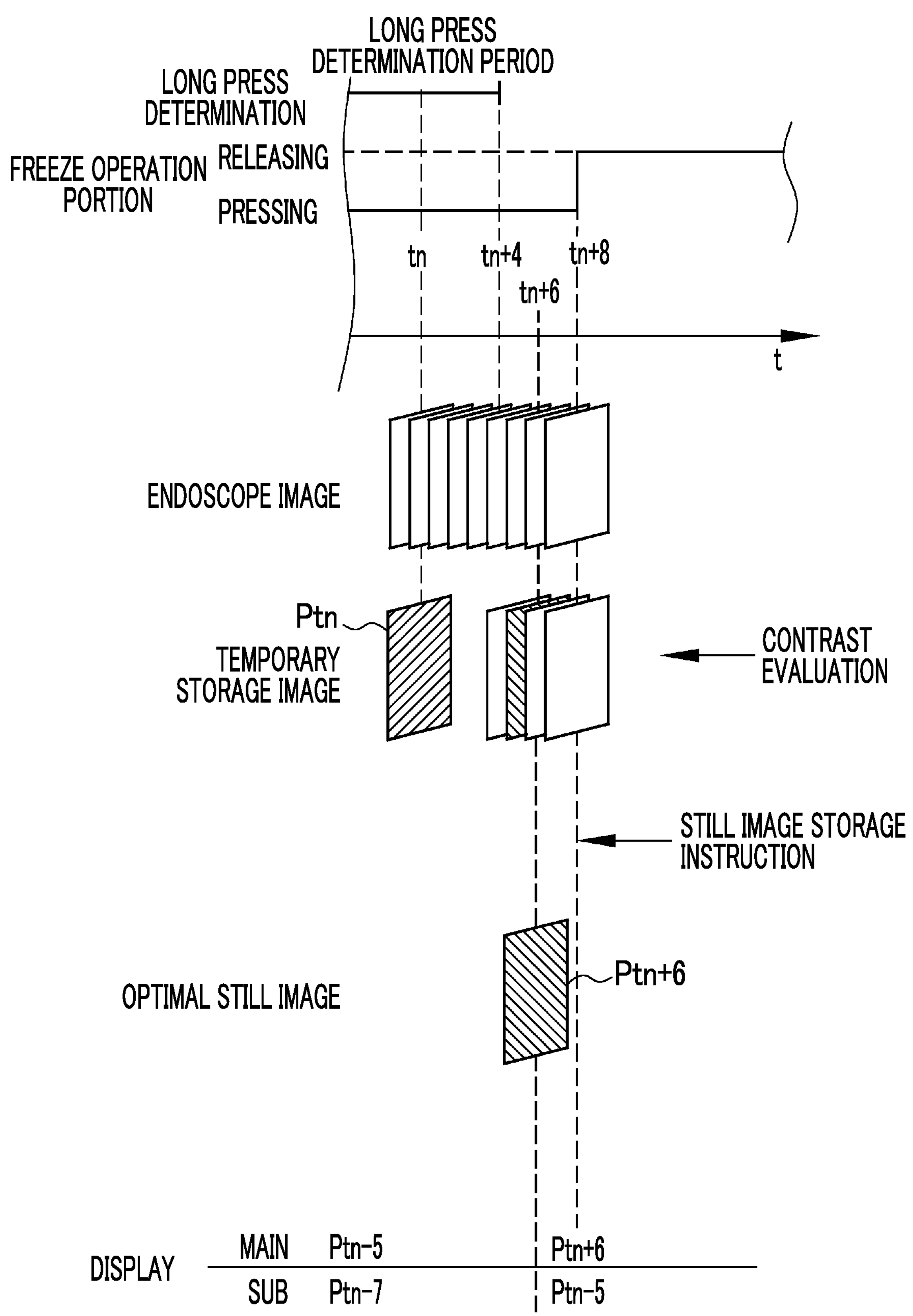
FIG. 18 is an explanatory diagram illustrating an example in which the optimal still image is displayed on a display.

As shown in FIG. 18, an endoscope image Ptn−5, which is the latest optimal still image stored up to that time, may be displayed on the main screen, and then, in a case where an optimal still image Ptn+6 is newly obtained, the endoscope image Ptn−5, which has been the optimal still image, may be updated and the optimal still image Ptn+6 may be displayed on the main screen. In addition, in a case where the optimal still image Ptn+6, which is the updated optimal still image, is displayed on the main screen, the endoscope image Ptn−5, which has been the optimal still image, is displayed on the sub screen. Therefore, in a case where the endoscope image Ptn−5 is displayed on the main screen, an endoscope image Ptn−7, which is the optimal still image before the endoscope image Ptn−5 is obtained, is displayed on the sub screen. After that, in a case where an endoscope image that is the optimal still image having a contrast evaluation value superior to that of the endoscope image Ptn+6 is obtained, the endoscope image Ptn−5 of the sub screen is updated, and the endoscope image Ptn+6 is displayed on the sub screen. Alternatively, a period in which the optimal still image is displayed on the main screen may be set as a display period set in advance, and the optimal still image may be displayed on the sub screen after this period. It is preferable that the endoscope image obtained in real time is displayed as a video during a period in which the optimal still image is not displayed on the main screen.

Only the main screen may be displayed on the display 18, only the optimal still image may be updated and displayed, two or more sub screens may be disposed and a plurality of past proper images may be displayed, or the like. In this case, a plurality of proper images selected from the latest proper images among the past proper images may be arranged and displayed in time series. By displaying the optimal still image and/or the proper still image on the display 18, the user can grasp how to operate the distance between the endoscope distal end portion and the subject to acquire a desired still image from the past proper still image, and the like. In addition, it is preferable because it is possible to grasp at a glance whether or not a desired still image has already been acquired, and the like.

Further, the endoscope system 10 may comprise a notification unit that notifies, in a case where the display 18 updates and displays the optimal still image and/or the proper still image, a user of the update. The notification unit may perform display on the display 18 of the endoscope system 10 or may be other means for allowing the user to recognize the notification, such as a sound. In the case of issuing notification through display on the display 18, it is preferable to issue notification through a method of allowing the user to recognize the display or the update at a glance by changing the color, the thickness, or the display form of the frame of the display of each still image on the display 18 for a certain period after the optimal still image and/or the proper still image is updated.

Figure 19:
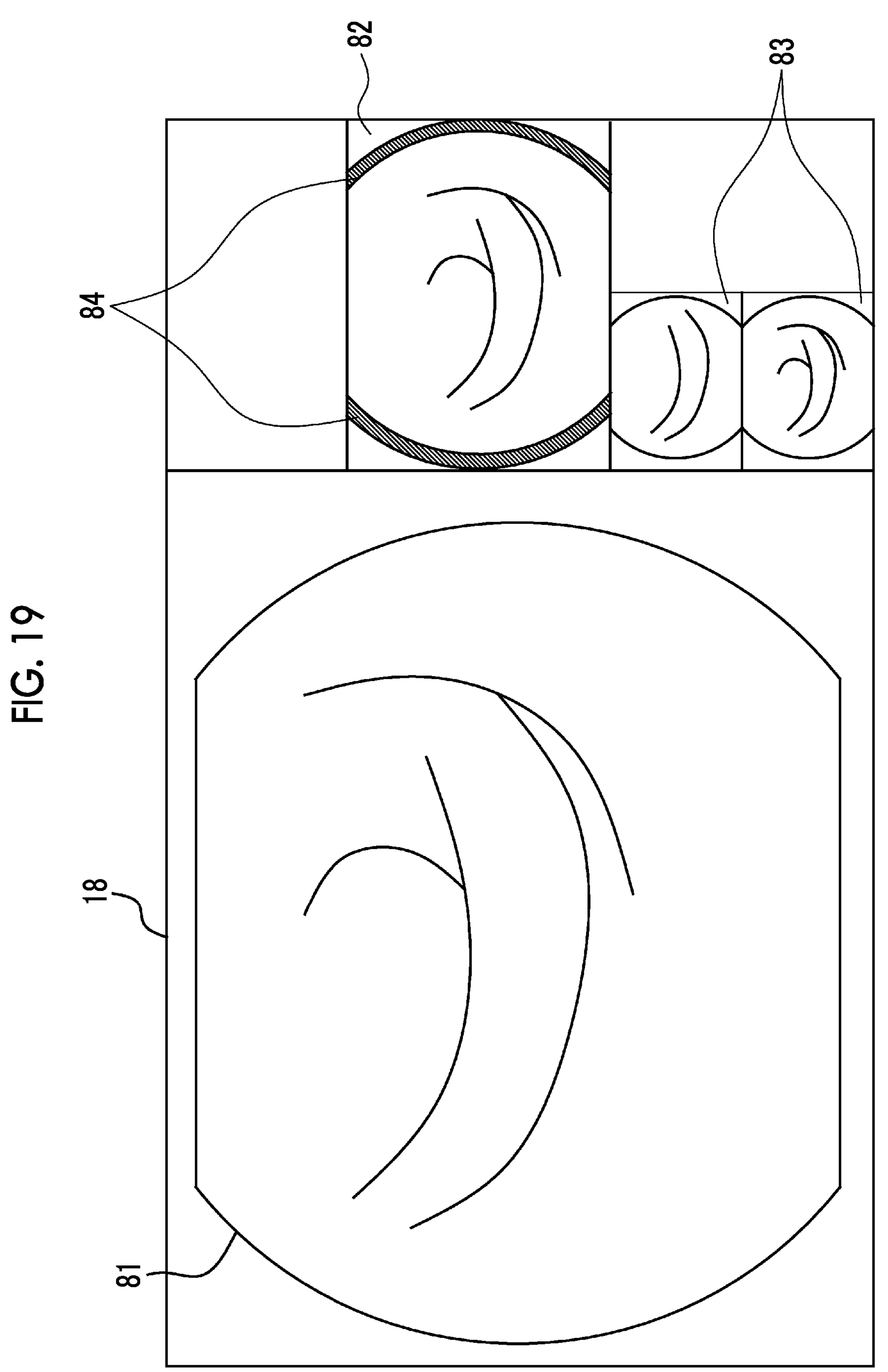
FIG. 19 is an explanatory diagram illustrating a case where update of the optimal still image is displayed on the display for a notification.

As shown in FIG. 19, for example, the display 18 comprises a video display screen 81, a still image display main screen 82, and a still image display sub screen 83. The video display screen 81 displays an endoscope image in real time. The optimal still image is displayed on the still image display main screen 82. In a case where the optimal still image is updated, the optimal still image is displayed by being surrounded by a still image display notification frame 84 which is a thick color line. Further, the still image display notification frame 84 may blink. As described above, a plurality of past optimal still images are displayed in time series on the still image display sub screen 83.

As described above, for example, in a case where the proper still image is updated and displayed, the user is notified of the update so that the user can pay attention to the display 18, and in a case where the updated proper still image is the still image desired by the user, the user releases the pressing of the freeze operation portion **12*f* at that point in time so that the proper still image updated and displayed on the display 18** can be stored as the optimal still image at a good timing.

In addition, in a case where the selection condition switching unit 72 switches between the first selection condition and the second selection condition, the notification unit may notify the user of the switching. Even in this case, as described above, for example, the notification can be issued by the display of the still image display notification frame 84 in the proper still image on the display 18.

It is preferable that the notification unit does not issue the notification in a case where the notification to the user is issued again within a minimum notification period set in advance. By setting the minimum notification period, it is possible to prevent the notification from being frequently issued and complicated.

In the above-described embodiment, the present invention is applied to the endoscope system that processes an endoscope image, but the present invention can also be applied to a medical image processing system that processes a medical image other than the endoscope image when a still image is stored. In addition, the present invention can also be applied to a case where an autofluorescence image obtained by capturing an autofluorescence image emitted from a subject by the irradiation of excitation light is used as an endoscope image, and the like, when a still image is stored.

In the above-described embodiment, the hardware structure of a processing unit that executes various kinds of processing, such as the central control unit 59, the image acquisition unit 51, the noise reduction unit 53, the signal processing unit 55, the image storage unit 56, the display control unit 57, and the video signal generation unit 58, which are provided in the processor device 16, is various processors to be described below. The various processors include a central processing unit (CPU) that is a general-purpose processor functioning as various processing units by executing software (programs), a programmable logic device (PLD) that is a processor of which a circuit configuration can be changed after manufacturing, such as a field programmable gate array (FPGA), a dedicated electrical circuit that is a processor having a circuit configuration exclusively designed to execute various kinds of processing, and the like.

One processing unit may be composed of one of these various processors or may be composed of a combination of two or more processors of the same type or different types (for example, a plurality of FPGAs or a combination of a CPU and an FPGA). Alternatively, a plurality of processing units may be composed of one processor. A first example in which a plurality of processing units are composed of one processor includes an aspect in which one or more CPUs and software are combined to constitute one processor and the processor functions as a plurality of processing units, as represented by a computer, such as a client or a server. A second example of the configuration includes an aspect in which a processor that realizes all the functions of a system including a plurality of processing units with one integrated circuit (IC) chip is used, as represented by a system on chip (SoC). As described above, various processing units are composed of one or more of the above various processors, as the hardware structure.

Furthermore, the hardware structures of the various processors are, more specifically, electrical circuitry having a form in which circuit elements, such as semiconductor elements, are combined.

EXPLANATION OF REFERENCES

10: endoscope system
12: endoscope
**12*a***: insertion part
**12*b***: operation part
**12*c***: bendable portion
**12*d***: distal end portion
**12*e***: angle knob
**12*f***: freeze operation portion
**12*g***: zoom operation portion
14: light source device
16: processor device
18: display
19: keyboard
20: light source unit
**20*a***: V-LED
**20*b***: B-LED
**20*c***: G-LED
**20*d***: R-LED
21: light source processor
**30*a***: illumination optical system
**30*b***: image capture optical system
41: light guide
42: illumination lens
43: objective lens
44: zoom lens
45: image capture sensor
46: CDS/AGC circuit
47: A/D converter
51: image acquisition unit
52: DSP
53: noise reduction unit
54: memory
55: signal processing unit
56: image storage unit
57: display control unit
58: video signal generation unit
59: central control unit
61: temporary storage unit
62: image evaluation unit
63: optimal still image storage unit
71: selection condition switching instruction reception unit
72: selection condition switching unit
73: temporary storage area
74: contrast evaluation unit
75: brightness evaluation unit
76: certainty factor evaluation unit
77: malignancy degree evaluation unit
78: still image storage instruction reception unit
79: optimal still image storage area
81: video display screen
82: still image display main screen
83: still image display sub screen
84: still image display notification frame
91: subject
db, db+c, dm: distance
T, t1 to t6, tn to tn+8: time
Pt2, Ptn, Ptn−7 to Ptn+7: endoscope image
ST100 to ST200: step

What is claimed is:

1. An endoscope system comprising:
an endoscope that images a subject; and
a processor,
wherein the endoscope includes an operation part,
the processor is configured to:
acquire an endoscope image obtained by imaging the subject with the endoscope for each frame;
temporarily store the endoscope image selected based on a first selection condition or a second selection condition in a temporary storage area as a temporary storage image;
perform image evaluation to assign an image evaluation value for each of the temporary storage images temporarily stored in the temporary storage area;
switch between the first selection condition and the second selection condition based on a user-issued selection condition switching instruction input through the operation part; and
store, based on a user-issued still image storage instruction input through the operation part, an optimal still image selected in accordance with the image evaluation value from the temporary storage images,
the processor is configured to temporarily store the selected endoscope image in the temporary storage area as the temporary storage image such that the number of temporarily storage images does not exceed a predetermined maximum number, the first selection condition includes:

a first A selection condition, which is applied in a case where the temporary storage image is temporarily stored in the temporary storage area in a number less than the maximum number, temporarily storing the endoscope image in the temporary storage area as the temporary storage image in an order of most recent imaging time until the maximum number is reached; and a first B selection condition, which is applied in a case where the maximum number of temporary storage images are temporarily stored in the temporary storage area, deleting the temporary storage image with an oldest imaging time, among the temporary storage images temporarily stored in the temporary storage area, from the temporary storage area and then temporarily storing the endoscope image in the temporary storage area as the temporary storage image in the order of the most recent imaging time, and the second selection condition includes:

a second A selection condition, which is applied in a case where the temporary storage image is temporarily stored in the temporary storage area in a number less than the maximum number, temporarily storing the endoscope image in the temporary storage area as the temporary storage image in an order of most recent imaging time until the maximum number is reached; and a second B selection condition, which is applied in a case where the maximum number of temporary storage images are temporarily stored in the temporary storage area, leaving only a proper still image selected in accordance with the image evaluation value from the temporary storage images in the temporary storage area as the temporary storage image and deleting an image except for the proper image from the temporary storage area, and then performing the second A selection condition.

2. The endoscope system according to claim 1, wherein the processor is configured to, in a case where acquisition of the endoscope image is started, temporarily store the endoscope image selected based on the first selection condition.

3. The endoscope system according to claim 1, wherein the operation part is configured to perform a first operation and a second operation, and the still image storage instruction is issued upon the second operation.

4. The endoscope system according to claim 3, wherein the operation part includes a momentary type switch, and the first operation is pressing of the momentary type switch, and the second operation is releasing of the pressed momentary type switch.

5. The endoscope system according to claim 3, wherein the operation part includes an alternate type switch, and the first operation is an operation of pressing the alternate type switch once to turn on the switch, and the second operation is an operation of pressing the alternate type switch again to turn off the switch.

6. The endoscope system according to claim 3, wherein the processor is configured to measure a period from the first operation to the second operation, and in a case where the period is equal to or longer than a determination period set in advance, the selection condition switching instruction is issued when the determination period has elapsed from the first operation.

7. The endoscope system according to claim 1, wherein the processor is configured to issue the selection condition switching instruction after issuing the still image storage instruction, in a case where the endoscope image is temporarily stored based on the second selection condition.

8. The endoscope system according to claim 1, wherein the second selection condition includes:

a second C selection condition, which is applied in a case where the maximum number of temporary storage images are temporarily stored in the temporary storage area, leaving only a proper still image selected in accordance with the image evaluation value from the temporary storage images in the temporary storage area as the temporary storage image and deleting an image except for the proper image from the temporary storage area, and then, after selecting and temporarily storing the endoscope image with the most recent imaging time in the temporary storage area as the temporary storage image, temporarily storing only a proper still image selected in accordance with the image evaluation value from the temporary storage images temporarily stored in the temporary storage area in the temporary storage area as the temporary storage image.

9. The endoscope system according to claim 1, further comprising:

a display configured to display the optimal still image and/or the proper still image, wherein the display is configured to, in a case where the optimal still image and/or the proper still image is displayed, update the optimal still image and/or the proper still image and display a latest optimal still image and/or a latest proper still image.

10. The endoscope system according to claim 9, wherein the display includes a main screen and a sub screen, and the optimal still image is displayed on the main screen for a display period set in advance and is displayed on the sub screen after the display period.

11. The endoscope system according to claim 9, wherein the processor is configured to:

in a case where the optimal still image and/or the proper still image is updated and displayed by the display, notify a user of the update.

12. The endoscope system according to claim 11, wherein the processor is configured to, in a case where the first selection condition and the second selection condition are switched, notify the user of the switching.

13. The endoscope system according to claim 11, wherein the processor is configured such that, in a case where an event requiring notification occurs again within a predetermined minimum notification period after a previous notification, no additional notification is issued.

14. The endoscope system according to claim 1, wherein the processor is configured to perform the image evaluation on contrast and/or brightness of the temporary storage image, and the image evaluation value is a value related to the contrast and/or the brightness of the temporary storage image.

15. The endoscope system according to claim 1, wherein the processor is configured to perform the image evaluation on a certainty factor and/or a malignancy degree related to a specific lesion of the subject appearing in the temporary storage image, and the image evaluation value is the certainty factor and/or the malignancy degree.

16. The endoscope system according to claim 1, wherein the processor is configured to set a threshold value for the image evaluation value, determine that the still image storage instruction is issued in a case where an image evaluation value equal to or greater than the threshold value is assigned to the temporary storage image, and store the temporary storage image as the optimal still image, without requiring a user-issued still image storage instruction.

17. The endoscope system according to claim 1, wherein the operation part includes a freeze operation portion.

18. An operation method for an endoscope system including an endoscope, which includes an operation part and images a subject, and a processor, the operation method comprising:

causing the processor to execute:

acquiring an endoscope image obtained by imaging the subject with the endoscope for each frame;

temporarily storing the endoscope image selected based on a first selection condition or a second selection condition in a temporary storage area as a temporary storage image;

performing image evaluation to assign an image evaluation value for each of the temporary storage images temporarily stored in the temporary storage area;

switching between the first selection condition and the second selection condition based on a user-issued selection condition switching instruction input through the operation part; and storing, based on a user-issued still image storage instruction input through the operation part, an optimal still image selected in accordance with the image evaluation value from the temporary storage images, wherein the method comprises causing the processor to execute temporarily storing the selected endoscope image in the temporary storage area as the temporary storage image such that the number of temporarily storage images does not exceed a predetermined maximum number, the first selection condition includes:

a first A selection condition, which is applied in a case where the temporary storage image is temporarily stored in the temporary storage area in a number less than the maximum number, temporarily storing the endoscope image in the temporary storage area as the temporary storage image in an order of most recent imaging time until the maximum number is reached; and a first B selection condition, which is applied in a case where the maximum number of temporary storage images are temporarily stored in the temporary storage area, deleting the temporary storage image with an oldest imaging time, among the temporary storage images temporarily stored in the temporary storage area, from the temporary storage area and then temporarily storing the endoscope image in the temporary storage area as the temporary storage image in the order of the most recent imaging time, and the second selection condition includes:

a second A selection condition, which is applied in a case where the temporary storage image is temporarily stored in the temporary storage area in a number less than the maximum number, temporarily storing the endoscope image in the temporary storage area as the temporary storage image in an order of most recent imaging time until the maximum number is reached; and a second B selection condition, which is applied in a case where the maximum number of temporary storage images are temporarily stored in the temporary storage area, leaving only a proper still image selected in accordance with the image evaluation value from the temporary storage images in the temporary storage area as the temporary storage image and deleting an image except for the proper image from the temporary storage area, and then performing the second A selection condition.

* * * * *